United States Patent [19]
Yabe et al.

[11] Patent Number: 5,722,933
[45] Date of Patent: Mar. 3, 1998

[54] CHANNELED ENDOSCOPE COVER FITTED TYPE ENDOSCOPE

[75] Inventors: Hisao Yabe; Minoru Yamazaki; Hideo Ito, all of Hachioji; Yoshio Tashiro, Hino; Yoshihiro Iida, Tama; Akira Suzuki; Osamu Tamada, both of Hachioji, all of Japan

[73] Assignee: Olympus Optical Co., Ltd., Tokyo, Japan

[21] Appl. No.: 806,707

[22] Filed: Feb. 27, 1997

Related U.S. Application Data

[63] Continuation of Ser. No. 353,995, Dec. 6, 1994, abandoned, which is a continuation of Ser. No. 25,333, Feb. 24, 1993, abandoned.

[30] Foreign Application Priority Data

| Jan. 27, 1993 | [JP] | Japan | 5-001830 U |
| Jan. 27, 1993 | [JP] | Japan | 5-001831 U |
| Feb. 1, 1993 | [JP] | Japan | 5-002269 U |

[51] Int. Cl.⁶ ............................................. A61B 1/04
[52] U.S. Cl. ........................ 600/123; 600/121; 600/154
[58] Field of Search .................................... 600/121, 122, 600/123, 124, 125, 154; 604/263; 206/363, 438, 439

[56] References Cited

U.S. PATENT DOCUMENTS

| 3,162,190 | 12/1964 | Gizzo . | |
| 3,709,223 | 1/1973 | Macalalad et al. | 604/163 X |
| 4,091,922 | 5/1978 | Egler | 206/439 X |
| 4,240,411 | 12/1980 | Hosono | 128/4 |
| 4,715,360 | 12/1987 | Akui et al. | 128/4 |
| 4,717,378 | 1/1988 | Perrault et al. | 604/111 X |
| 4,721,097 | 1/1988 | D'Amelio | 128/4 |
| 4,741,326 | 5/1988 | Sidall et al. | 128/4 |
| 4,809,679 | 3/1989 | Shimonaka | 128/4 |
| 4,886,049 | 12/1989 | Darras | 128/4 |
| 4,991,564 | 2/1991 | Takahashi et al. | 128/4 |
| 5,050,585 | 9/1991 | Takahashi | 128/4 |
| 5,144,942 | 9/1992 | Decarie et al. | 128/4 |

FOREIGN PATENT DOCUMENTS 2-54734 11/1990 Japan .

*Primary Examiner*—Beverly M. Flanagan
*Attorney, Agent, or Firm*—Armstrong, Westerman, Hattori, McLeland & Naughton

[57] ABSTRACT

A cover-fit endoscope can be used while being covered with a cover so that it is watertight. An appliance channel is extended through the cover and an appliance insertion inlet of the channel is open. This opening of the appliance insertion inlet is provided with an integral appliance plug. It is therefore possible to prevent the contaminated appliance plug from being fitted to the sterilized cover by mistake, and also to prevent leakage of the body fluids. Thus, the cover-fit endoscope is kept from contamination. The cover and the appliance plug are both discarded after use. The need for washing and disinfecting the cover-fit endoscope is eliminated, and use of the sterilized appliance plug is always ensured to reduce a fear of infection.

14 Claims, 16 Drawing Sheets

UNWOUND WHEN INSERTED
WOUND WHEN EXTRACTED

1

CHANNELED ENDOSCOPE COVER FITTED TYPE ENDOSCOPE

This application is a continuation of application Ser. No. 08/353,995, filed Dec. 6, 1994, now abandoned, which is a continuation of application Ser. No. 08/025,333, filed Feb. 24, 1993 now abandoned.

BACKGROUND OF THE INVENTION

1. Field of the Invention

The present invention relates to a channeled endoscope cover fitted type endoscope which employs a channeled endoscope cover for preventing contamination of the endoscope.

2. Description of the Related Art

Endoscope examination requires use of clean endoscopes sufficiently washed and disinfected prior to the examination.

After having been used in the body cavities of patients, endoscopes are washed and disinfected. Washing and disinfection operations are very time consuming and cannot achieve an expected effect unless fully completed. In an endoscope examination, therefore, it has been recently proposed to use endoscopes fitted with disposable endoscope covers instead of conventional endoscopes being repeatedly used after washing and disinfection.

Such an endoscope cover fitted type endoscope comprises, in combination, an endoscope cover for covering the outer periphery of an endoscope insert etc. and a cover-fit endoscope which is inserted in the endoscope cover. Examples of the endoscope cover fitted type endoscope are described in U.S. Pat. No. 4,646,722 (Japanese Patent Publication No. 2-54734) and U.S. Pat. No. 3,162,190, for instance.

The cover-fit endoscope to be fitted with the endoscope cover has an insert typically provided with an image sensing system or observation optical system and a light guide fiber.

An appliance channel and other channels used for supplying air and water may be contaminated by body fluids or the like, and are hard to carry out washing and disinfection because of their long and narrow form. For this reason, the endoscope cover is formed with those channels open at one or both ends end.

In use of the cover fitted type endoscope, its insert is washed and disinfected beforehand. The endoscope cover, also washed and disinfected beforehand, is then fitted over the endoscope insert etc. and, in this covered condition, the endoscope is inserted into the body cavity of a patient. After use, the endoscope cover is removed and discarded. By so disposing of the endoscope cover for each patient, the endoscope does not require repeated washing and disinfecting and is kept highly hygienic. The endoscope can be used continually with no need for washing and disinfection.

A conventional non-covered endoscope has an appliance channel closed by an appliance plug to prevent contamination by filth and so on. The conventional appliance plug is releasably attached and, for each operation or treatment, it is removed from an endoscope body, followed by washing and disinfection.

The cover fitted type endoscope similarly has an appliance channel which has an opening releasably fitted with an appliance plug to prevent contamination by filth and so on. Then, as with the non-covered endoscope, the appliance plug used in the cover fitted type endoscope is also removed from an endoscope body, followed by washing and disinfection. There occur no problems if the appliance plug is sufficiently washed and disinfected. However, insufficient washing and disinfection causes a risk of infection.

It is also difficult to perform sufficient washing and disinfection in a short period of time between operations. Further, a risk of being accidentally contaminated during the period from washing and disinfection to reattachment is high. There is another fear that a contaminated appliance plug may be attached by mistake to the channel opening already sterilized.

In short, for the cover fitted type endoscope, the appliance plug is removed from the endoscope body and subjected to washing and disinfection for each operation. At this time, sufficient washing and disinfection are difficult to finish in a short period of time between operations, while insufficient washing and disinfection accompanies a risk of causing infection. Another fear of attaching a contaminated appliance plug also exists.

Meanwhile, a fluid controller provided with an air supply source and a water supply source, for instance, is connected to lines or passages such as air and water supply tubes so that air, water, etc. are supplied through the respective lines.

When the cover-fit endoscope is removed from the endoscope cover after examination, the air and water supply lines, etc. are first removed from the fluid controller. The cover-fit endoscope is then removed from the endoscope cover. At this time, there is a fear that filth and so on leaking through open ends of the fluid lines may contaminate the cover-fit endoscope.

Particularly, in the type that the lines in the endoscope cover are inserted to respective line insertion channels in the cover-fit endoscope, the interior of these channels is contaminated. Therefore, when lines in an endoscope cover used for the next examination are inserted to the respective contaminated channels the interior of the line so far kept clean is also contaminated.

As mentioned above, since the channels of the endoscope cover serving as various-purpose lines have openings, there is a risk that fluids, filth and so on may leak through the openings and contaminate the cover-fit endoscope when the cover is removed from it. Another risk also exists that contaminated members may be fitted by mistake to sterilized members. There is an additional possibility that sterilized members may be accidentally contaminated prior to starting examination. These points are opposed to the intrinsic purpose of using covers. It is hence important to prevent such risks.

SUMMARY OF THE INVENTION

An object of the present invention is to prevent components of a cover from being scattered, and eliminate undesired contamination of the components or mistaken fitting of the contaminated components.

Another object of the present invention is to eliminate the need for washing and disinfecting a cover-fit endoscope, and also to eliminate contamination of an appliance plug and mistaken fitting of the contaminated appliance plug, thereby preventing infection.

Still another object of the present invention is to prevent filth from leaking through open ends of channels to contaminate the cover-fit endoscope and cause infection.

Still another object of the present invention is to prevent contamination of insertion channels of the endoscope to which cover channels are inserted.

Still another object of the present invention is to provide a stout cover which will not be torn, thereby preventing contamination of the cover-fit endoscope and the possibility of a resulting infection.

Still another object of the present invention is to enable recognition of use/non-use of the cover and prevent mistaken fitting of the cover which might be contaminated.

With one preferred form of the present invention, in a channeled endoscope cover fitted type endoscope comprising a channeled endoscope cover having a channel open at least at its proximal end, and a channeled endoscope cover fitting endoscope to be covered by the channeled endoscope cover, a member for covering the proximal end opening of the channel is provided on the channeled endoscope cover.

With another form of the present invention, in a channeled endoscope cover fitted type endoscope, the channeled endoscope cover has a sheath cover covering the channel, the sheath cover is formed of a plurality of layers being each anisotropic in the tearing strength, and the plurality of layers are arranged to exhibit the tearing strength in different directions from one another.

With still another form of the present invention, in a channeled endoscope cover fitted type endoscope, the sheath cover is formed to be capable of winding and unwinding.

With still another form of the present invention, in a channeled endoscope cover fitted type endoscope, components of the channeled endoscope cover are all contained in one package means.

With still another form of the present invention, in a channeled endoscope cover fitted type endoscope, the channeled endoscope cover includes means for providing a confirmed indication based on whether or not the cover has been used.

Other features and advantages of the present invention will be fully apparent from the following detailed description.

BRIEF DESCRIPTION OF THE DRAWINGS

FIGS. 1 and 2 relate to a first embodiment of the present invention in which: FIG. 1 is an overall appearance view of a channeled endoscope cover fitted type endoscope apparatus.

FIG. 2 is a side sectional view of the distal end side of the channeled endoscope cover fitted type endoscope.

FIGS. 3 and 4 relate to a second embodiment of the present invention in which: FIG. 3 is a side sectional view of the distal end side of a channeled endoscope cover fitted type endoscope.

FIG. 4 is an explanatory view showing a packed condition of a cover and other components.

FIGS. 5 to 8 relate to a third embodiment of the present invention in which: FIG. 5 is an overall appearance view of a channeled endoscope cover fitted type endoscope apparatus.

FIG. 6 is an appearance view of a channeled endoscope cover.

FIG. 7 is an appearance view of an endoscope to be fitted with the channeled endoscope cover.

FIG. 8 is a view of showing the construction of a line end, including a principal part of this embodiment.

FIGS. 13 to 19 relate to a seventh embodiment of the present invention in which: FIG. 13 is an overall appearance view of a channeled endoscope cover fitted type endoscope apparatus.

FIG. 15 is an explanatory view showing a state that a line cover tube is fitted to lines in an insert cover portion.

FIG. 16 is an explanatory view showing a state that the cover is being fitted to the cover-fit endoscope.

FIG. 17 is an explanatory view showing a state that the cover has been completely fitted over the cover-fit endoscope.

FIG. 18 is an explanatory view showing a state when the cover-fit endoscope is extracted from the cover.

FIG. 19 is a side sectional view showing a modification of the cover fitted type endoscope.

DETAILED DESCRIPTION OF THE PREFERRED EMBODIMENTS

Hereinafter, embodiments of the present invention will be described with reference to the drawings.

Figure 1:
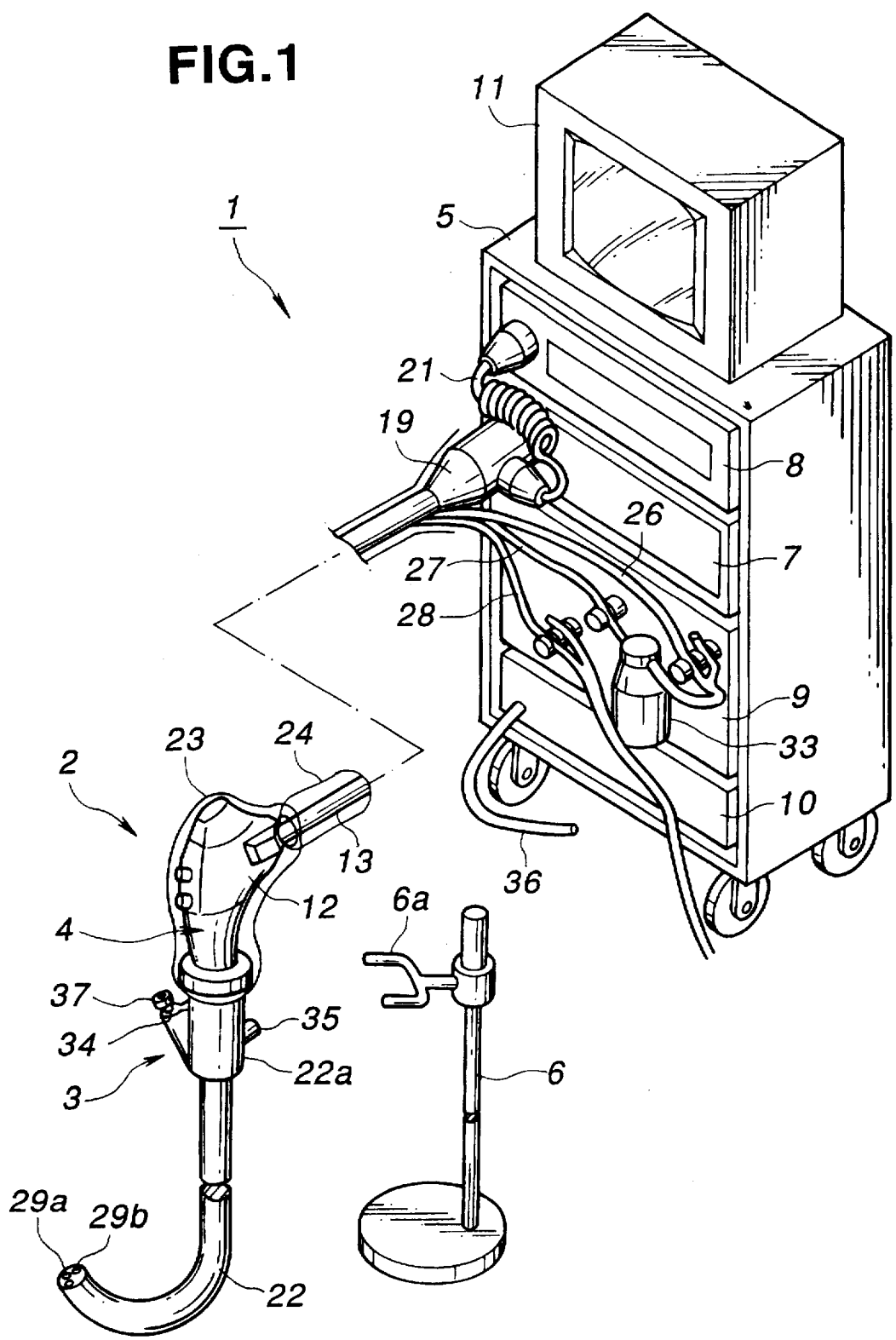
Figure 2:
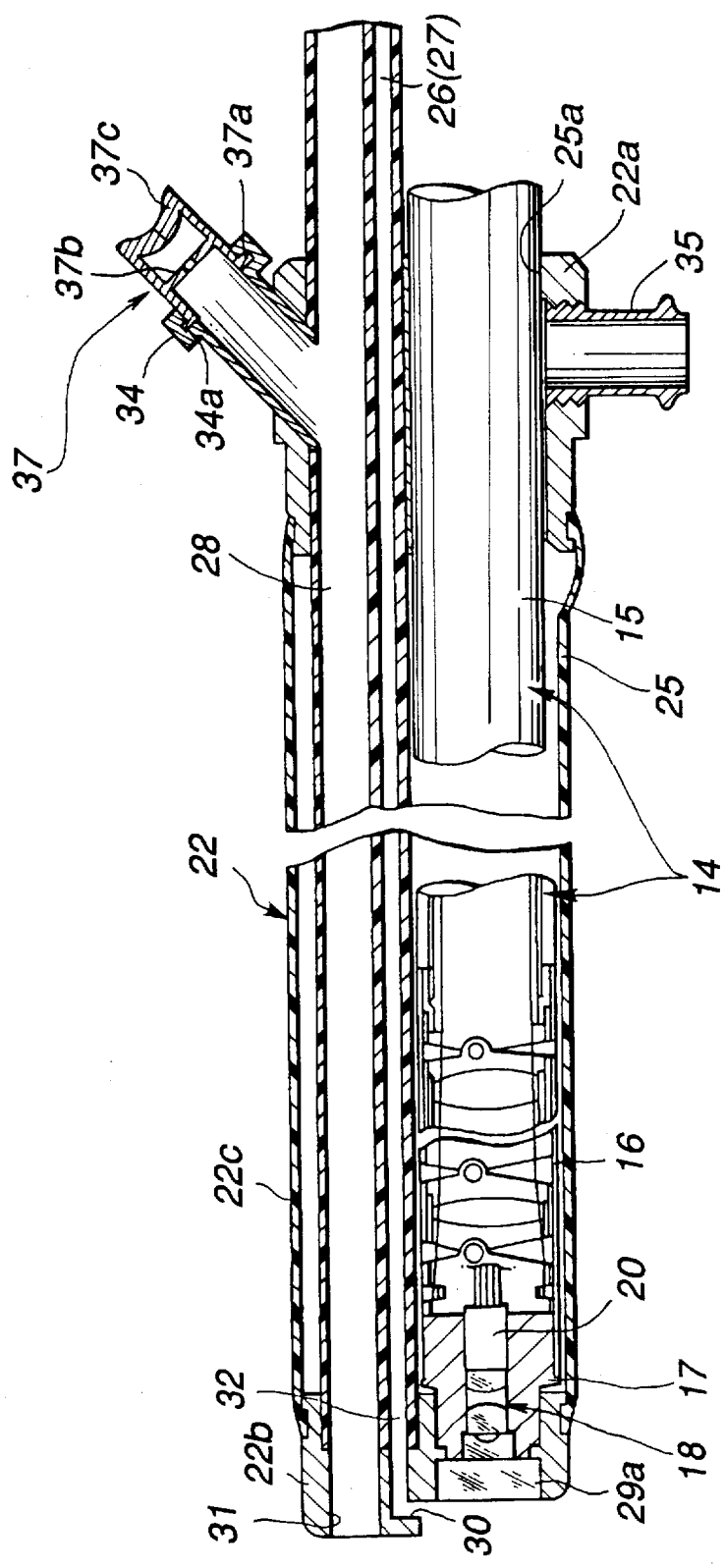

FIGS. 1 and 2 relate to a first embodiment of the present invention in which FIG. 1 is an overall appearance view of a channeled endoscope cover fitted type endoscope apparatus, and FIG. 2 is a side sectional view of the distal end side of the channeled endoscope cover fitted type endoscope.

An endoscope apparatus 1 shown in FIG. 1 includes a channeled endoscope cover fitted type endoscope (hereinafter abbreviated as a cover fitted type endoscope) 2.

The cover fitted type endoscope 2 comprises, in combination, a channeled endoscope cover (hereinafter abbreviated as a cover) 3 and an endoscope to be fitted with the channeled endoscope cover (hereinafter abbreviated as a cover-fit endoscope) 4. The cover 3 covers an insert etc. of the cover-fit endoscope 4 to eliminate the need of washing and disinfecting the endoscope after examination.

The endoscope apparatus 1 comprises the cover fitted type endoscope 2, a cart 5 for housing various peripheral equipment therein to which the cover fitted type endoscope 2 is connected, and a cover holder 6 for holding the cover fitted type endoscope 2.

As shown in FIG. 1, the cart 5 for housing various peripheral equipment therein houses, for instance, a light source unit 7, a video processor 8, a fluid controller 9, and an expander for the channeled endoscope cover (hereinafter abbreviated as an expander) 10. A monitor 11 is placed on a top plate of the cart 5.

The light source unit 7 supplies an illumination light to the cover-fit endoscope 4 of the cover fitted type endoscope 2. The video processor 8 is connected to the electronic cover-fit endoscope 4 for converting an electric signal from the endoscope 4 into a standard video signal and outputting it to the monitor 11. The monitor 11 receives the video signal and displays an endoscope image.

The fluid controller 9 carries out supply of air and water, etc. through later-described lines provided in the cover 3. To this end, the fluid controller 9 includes a water supply source 33, an air supply source (not shown), etc. and the lines connected to these water and air supply sources are controlled by solenoid valves to selectively open and close.

The expander 10 supplies air to the cover 3 for expanding the same. This expansion of the cover 3 allows the cover-fit endoscope 4 to be easily inserted and extracted.

The cover-fit endoscope 4 comprises an operating unit 12 shown in FIG. 1, a universal cord 13 extending from one side of the operating unit 12, and an insert 14 connected to the operating unit 12, the distal end side of the insert 14 being shown in FIG. 2. The insert 14 of the cover-fit endoscope 4 comprises, as shown in FIG. 2, a flexible tube portion 15, a bendable bending portion 16, and a hard distal end portion 17 arranged in this order from its proximal end adjacent the operating unit 12 toward its distal end.

The insert 14 of the cover-fit endoscope 4 is formed to have, for instance, a semicircular or D-shaped cross-section. This configuration is intended to secure a space for later-described lines formed in the cover and facilitate insertion of those lines while realizing the thinner insert.

In the distal end portion 17 of the cover-fit endoscope 4, there are arranged an illumination optical system (not shown) and an objective optical system 18.

An exiting end of a light guide fiber (not shown) is arranged at a rear end of the illumination optical system, the light guide fiber being inserted through the insert 14, the operating unit 12 and the universal cord 13.

A connector 19 is provided at a proximal end of the universal cord 13 and releasably connected to the light source unit 7. The illumination light from the light source unit 7 is introduced to an incoming end of the light guide fiber.

At a rear end of the objective optical system 18, as shown in FIG. 2, there is arranged a solid state image sensor 20 for converting an incoming optical image into an electric signal. The electric signal output from the solid state image sensor 20 is applied to the video processor 8 such as via a signal cord 21 extending from one side of the connector 19 shown in FIG. 1.

The cover 3 to be fitted over the cover-fit endoscope 4 comprises, as shown in FIG. 1, an insert cover portion 22, an operating unit cover portion 23, and a universal cord cover portion 24. The insert cover portion 22 of the cover 3 covers the insert 14 of the cover-fit endoscope 4. The operating unit cover portion 23 of the cover 3 covers the operating unit 12 of the cover-fit endoscope 4 and three later-described lines. Further, the universal cord cover portion 24 of the cover 3 covers the universal cord 13 of the cover-fit endoscope 4 and the three later-described lines. The cover-fit endoscope 4 is entirely fitted with the cover 3 and used for examination in a watertight covered condition.

Additionally, when the insert cover portion 22 is fitted to the cover-fit endoscope 4, the cover holder 6 holds, by its arm 6a, a later-described mouth portion of the insert cover portion 22. This enables the endoscope to be held without touching the cover 3 by a hand, which is desirable from a hygienic standpoint. Also, the fitting operation is made easier.

FIG. 2 shows a side sectional view in a state in which the insert cover portion 22 of the cover 3 is fitted over the cover-fit endoscope 4.

The insert cover portion 22 is of an elongate shape and has a mouth portion for fixing an endoscope operating unit (hereinafter abbreviated as a mouth portion) 22a at the proximal end and a distal end portion 22b which are both formed of hard material. The region of the insert cover portion 22 between the mouth portion 22a and the distal end portion 22b is covered with an insert cover sheath 22c formed of flexible material.

Further, the insert cover portion 22 has formed therein an endoscope insertion channel 25 to which the insert 14 can be inserted, as well as an air supply line 26, a water supply line 27 and a suction line 28, these lines being each in the form of a tube.

On the proximal end side of the endoscope insertion channel 25, an opening 25a for inserting the insert 14 therethrough is formed in the mouth portion 22a. The opening 25a of the endoscope insertion channel 25 is formed to have such a diameter that the mouth portion 22a closely contacts the endoscope insert 14. The distal end portion 22b is closed at the endoscope insertion channel 25 to isolate the insert 14 of the cover-fit endoscope 4 from the external environment so that it is airtight.

At the distal end portion 22b of the insert cover portion 22, as shown in FIG. 1, transparent windows 29a, 29b are provided to close the distal end of the endoscope insertion channel 25. These windows 29a, 29b are arranged at positions respectively facing the observation optical system 18 and the illumination optical system of the cover-fit endoscope 4.

Also, at the distal end portion 22b of the insert cover portion 22, there are formed an air/water supply nozzle 30 opened toward the window 29a, and an opening 31. The air/water supply nozzle 30 is connected in fluid communication with an air/water supply line 32 into which the air supply line 26 and the water supply line 27 join together near the distal end of the insert cover portion 22. The opening 31 is connected in fluid communication with the suction line 28.

The air supply line 26, the water supply line 27 and the suction line 28 are further extended from the mouth portion 22a toward the proximal side and are open at their ends. As shown in FIG. 1, the air supply line 26 is connected in fluid communication with the air supply source (not shown) of the fluid controller 9. The water supply line 27 is connected in fluid communication with the air supply source via a water supply tank 33 as the water supply source. Further, the suction line 28 is connected in fluid communication with a suction bottle (not shown) and a suction source (not shown).

The mouth portion 22a is provided with an appliance insertion inlet 34 and an expansion tube mouth 35 projecting from opposite sides. The expansion tube mouth 35 has its inner passage communicated with the endoscope insertion channel 25. An expansion tube 36 connected to the expander 10 is in turn releasably connected to the expansion tube mouth 35.

The appliance insertion inlet 34 projects rearward in an axial direction from the insert cover portion 22. An inner passage of the appliance insertion inlet 34 is open at a projected end and communicated at the other end with the suction line 28. Thus, the suction line 28 doubles as an appliance channel in the distal end side.

At the projected end of the appliance insertion inlet 34, a substantially tubular appliance plug 37 is provided integrally with the appliance insertion inlet 34.

The appliance insertion inlet 34 has a circumferential groove 34a formed in its inner end surface. On the other hand, the appliance plug 37 is formed from an elastic member and has a flange 37a projecting from the outer periphery of its one end. The appliance plug 37 is elastically deformed so as to engage in the groove 34a formed in the appliance insertion inlet 34.

The appliance plug 37 also has a disk portion 37b formed therein at an intermediate position and having a hole with a smaller diameter than an outer diameter of the appliance inserted through the opening defined on the side of the flange 37a. The appliance plug 37 further has a slit portion 37c formed at the other end and having a slit. Thus, the appliance can be inserted through the elastically deformed appliance plug 37 while penetrating the slit of the slit portion 37c and the small hole of the disk portion 37b. With the appliance not inserted, the slit is tightly closed to isolate the inner passage of the appliance plug 37 from the external environment.

Note that the appliance plug 37 may be integrated with the appliance insertion inlet 34 such as by bonding, hot fusing or molding other than engaging.

In this embodiment, since the appliance plug 37 is provided integrally with the appliance insertion inlet 34 of the insert cover portion 22, there is no fear that the contaminated appliance plug may be used by mistake. Also, the slit portion 37c of the appliance plug 37 serves to prevent intrusion of foreign matters and leakage of filth and so on. Further, since the appliance plug 37 is discarded after use along with the cover 3, this embodiment can eliminate the need of washing and disinfecting the endoscope, prevent contamination of the appliance plug and a mistaken fitting of the contaminated appliance, as well as reducing a fear of infection.

Figure 3:
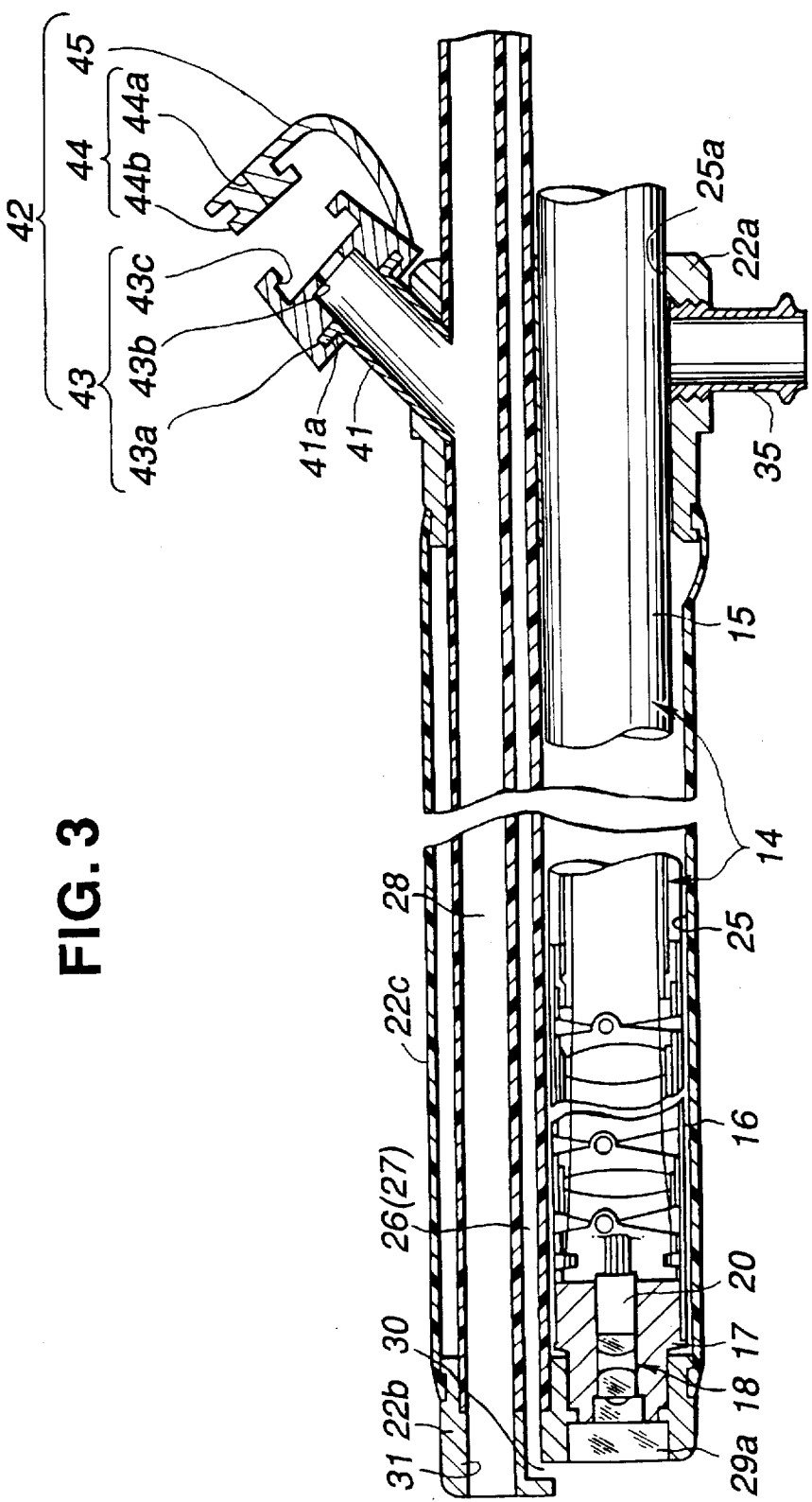
Figure 4:
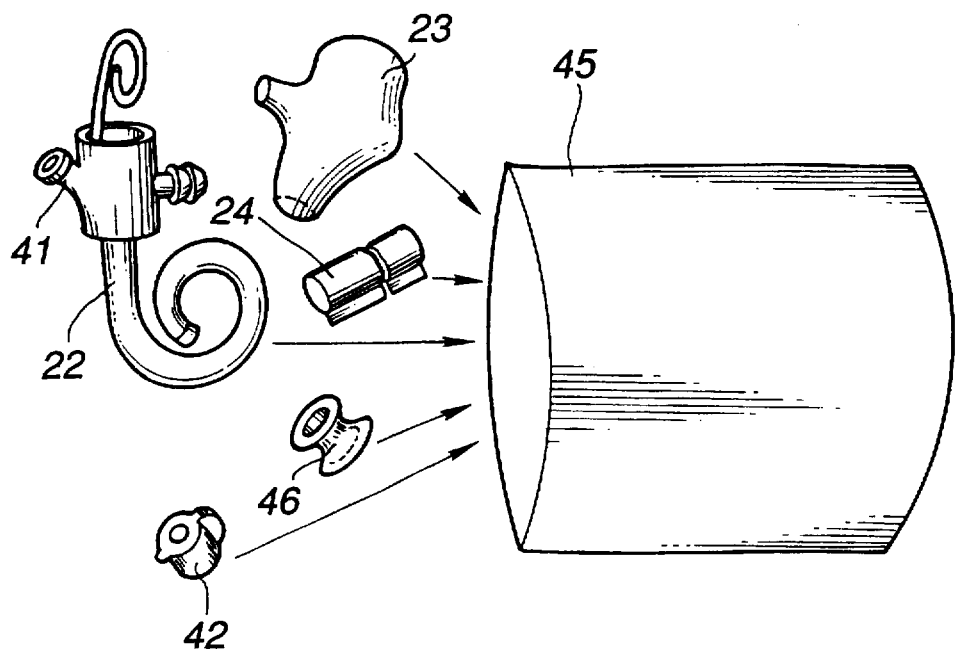

FIGS. 3 and 4 relate to a second embodiment of the present invention in which FIG. 3 is a side sectional view of the distal end side of a channeled endoscope cover fitted type endoscope, and FIG. 4 is an explanatory view showing a packed condition of a cover and other components.

In the second embodiment, as shown in FIG. 3, an appliance plug 42 is externally engaged over an appliance insertion inlet 41. Also, the second embodiment is different from the first embodiment in that an engagement projection 44b integral with the appliance plug 42 is releasably fitted to an engagement recess 43c of the appliance plug 42. Other similar construction and operation to those in the first embodiment will not be explained again by denoting the same parts at the same reference numerals. The entire construction of the endoscope apparatus is also assumed to be similar to that shown in FIG. 1.

As shown in FIG. 3, a flange 41a is formed at a projected end of the appliance insertion inlet 41. The appliance plug 42 is formed from an elastic member. The appliance plug 42 comprises a first plug body 43, a second plug body 44, and an arm 45 coupling the first plug body 43 and the second plug body 44. The first plug body 43 has a circumferential groove 43a formed near one end of its inner passage and engaging the flange 41a. The first plug body 43 also has a disk portion 43b formed therein at an intermediate position of the inner passage and having a hole with a smaller diameter than an outer diameter of the appliance inserted through the inner passage. Further, the first plug body 43 has the engagement recess 43c formed at the other end for engaging the second plug body 44.

The second plug body 44 is provided with a slit portion 44a having a slit formed axially of the inner passage, and with the engagement projection 44b formed at one end to engage the engagement recess 44c of the first plug body 43.

Next, FIG. 4 shows a packed condition of the appliance plug 42, the cover 3 and so on.

A cover package 45 shown in FIG. 4 is to pack the appliance plug 42, the cover 3 and so on therein for protecting them from contamination.

The cover package 45 is formed of air permeable material, but the material has holes of less than 0.2 μm, for instance, so that germs cannot penetrate the material. The cover package 45 accommodates the insert cover portion 22, the operating unit cover portion 23, the universal cord cover portion 24, a mouth piece 46, etc. After containing the cover and other components, the cover package 45 is put in a sterilizer (not shown) for sterilization. All the cover and other components necessary for each examination or treatment can be thereby kept in a sterilized condition. Further, since the cover package 45 contains all the cover and other components necessary for each examination or treatment, it is possible to prevent any of the cover and other components from being missing or from being not fitted in place.

With this embodiment, the sterilized appliance plug is packed in the cover package and the packed components are all fitted in place before examination. Accordingly, it is only required to fit the packed components one by one, meaning no possibility of using a non-sterilized appliance plug by mistake.

In addition, the cover package can be discarded in a condition that it contains the cover components, the mouth piece 46, etc. together. This is effective in preventing the used components from being erroneously taken as the sterilized components before use.

When disposing of the cover and so on, they can be discarded together in a condition of being contained in the cover package.

Thus, the use of the cover package facilitates part management.

Note that the appliance plug may be fitted to the appliance insertion inlet of the cover beforehand and then packed in the cover package.

The other construction, operation and advantages are similar to those in the first embodiment and will not be described again.

Figure 5:
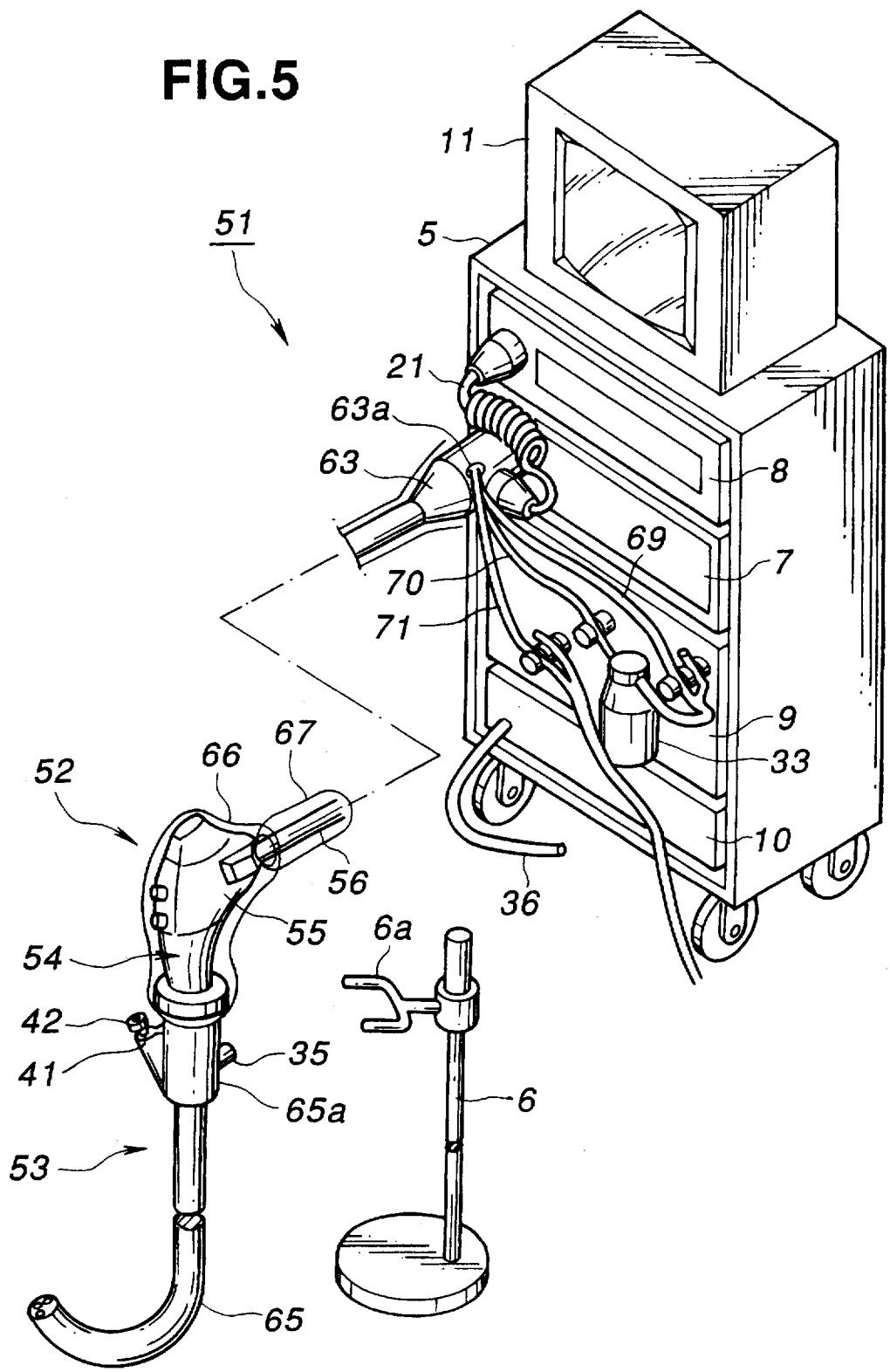
Figure 6:
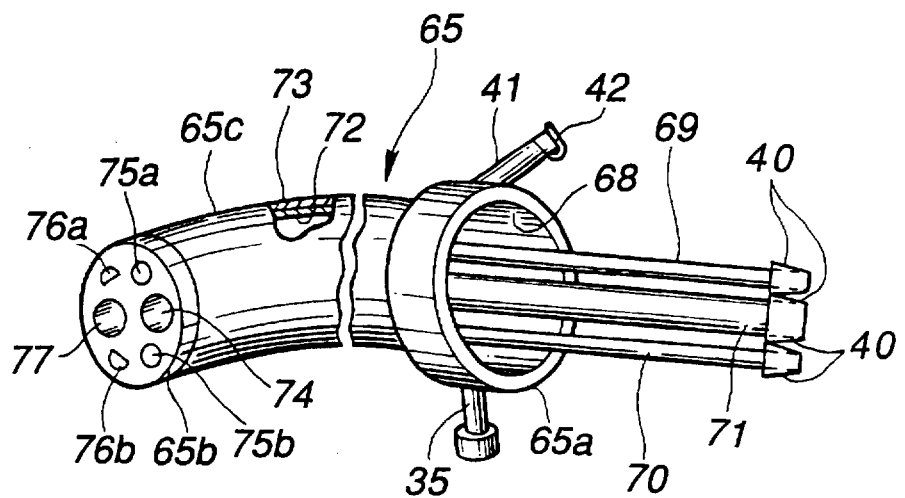
Figure 7:
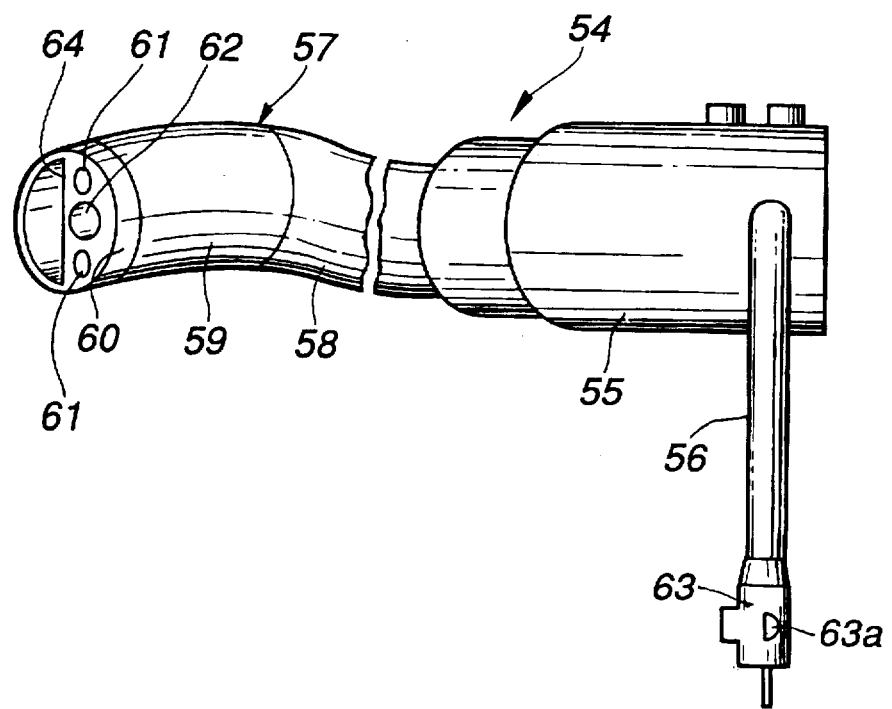

FIGS. 5 to 8 relate to a third embodiment of the present invention in which: FIG. 5 is an overall appearance view of a channeled endoscope cover fitted type endoscope apparatus, FIG. 6 is an appearance view of a channeled endoscope cover, FIG. 7 is an appearance view of an endoscope to be fitted with the channeled endoscope cover, and FIG. 8 is a view of showing the construction of a line end, including a principal part of this embodiment.

An endoscope apparatus 51 shown in FIG. 5 includes a channeled endoscope cover fitted type endoscope (hereinafter abbreviated as a cover fitted type endoscope) 52.

The cover fitted type endoscope 52 comprises, in combination, a channeled endoscope cover (hereinafter abbreviated as a cover) 53 and an endoscope to be fitted with the channeled endoscope cover (hereinafter abbreviated as a cover-fit endoscope) 54. The cover 53 covers an insert etc. of the cover-fit endoscope 54 to eliminate any need for washing and disinfecting the endoscope after examination.

The endoscope apparatus 51 comprises the cover fitted type endoscope 52, a cart 5 for housing various peripheral equipment therein to which the cover fitted type endoscope 52 is connected, and a cover holder 6 for holding the cover fitted type endoscope 52.

As shown in FIG. 5, the cart 5 for housing various peripheral equipment therein houses, for instance, the light source unit 7, the video processor 8, the fluid controller 9, and the expander 10. The monitor 11 is placed on a top plate of the cart 5.

The light source unit 7 supplies an illumination light to the cover-fit endoscope 54 of the cover fitted type endoscope 52.

The video processor 8 is connected to the electronic covered-fit endoscope 54 for converting an electric signal from the endoscope 54 into a standard video signal and outputting it to the monitor 11. The monitor 11 receives the video signal and displays an endoscope image.

The fluid controller 9 carries out supply of air and water, etc. through later-described lines provided in the cover 53. To this end, the fluid controller 9 includes a water supply source 33, an air supply source (not shown), etc. and the lines connected to these water and air supply sources are controlled by solenoid valves to selectively open and close.

The expander 10 supplies air to the cover 53 for expanding the same. This expansion of the cover 53 allows the cover-fit endoscope 54 to be easily inserted and extracted.

The cover-fit endoscope 54 comprises, as shown in FIG. 7, an operating unit 55, a universal cord 56 extending from one side of the operating unit 55, and an insert 57 connected to the operating unit 55. The insert 57 of the cover-fit endoscope 54 is formed into an elongate cylindrical shape. Accordingly, the same bending structure as used in conventional non-covered endoscopes can also be applied to the cover-fit endoscope 54.

The insert 57 of the cover-fit endoscope 54 comprises, as shown in FIG. 7, a flexible tube portion 58, a bendable bending portion 59, and a hard distal end portion 60 arranged in this order from its proximal end adjacent the operating unit 55 toward its distal end.

In the distal end portion 60 of the cover-fit endoscope 54, there are arranged illumination optical systems 61, 61 and an objective optical system 62.

An exiting end of a light guide fiber (not shown) is arranged at rear ends of the illumination optical systems 61, 62, the light guide fiber being inserted through the insert 57, the operating unit 55 and the universal cord 56.

A connector 63 is provided at a proximal end of the universal cord 56 and releasably connected to the light source unit 7. The illumination light from the light source unit 7 is introduced to an incoming end of the light guide fiber.

In the distal end portion 60 of the cover-fit endoscope 54, there is formed an opening of a line insertion channel 64 having a semicircular or D-shaped cross-section. A plurality of later-described lines formed in the cover 53 are inserted through the line insertion channel 64. The line insertion channel 64 is communicated with a proximal end opening 63a formed in one side of the connector 63 through the insert 57, the operating unit 55 and the universal cord 56.

At a rear end of the objective optical system 62, there is arranged a solid state image sensor (not shown) for converting an incoming optical image into an electric signal. The electric signal output from the solid state image sensor is applied to the video processor 8 such as via a signal cord 21 extending from one side of the connector 63 shown in FIG. 5.

The cover 53 to be fitted over the cover-fit endoscope 54 comprises, as shown in FIG. 5, an insert cover portion 65, an operating unit cover portion 66, and a universal cord cover portion 67. The insert cover portion 65 of the cover 53 covers the insert 57 of the cover-fit endoscope 54. The operating unit cover portion 66 of the cover 53 covers the operating unit 55 of the cover-fit endoscope 54. Further, the universal cord cover portion 67 of the cover 53 covers the universal cord 56 of the cover-fit endoscope 54. The cover-fit endoscope 54 is entirely fitted with the cover 53 and used for examination in a covered condition which is watertight.

Additionally, when the insert cover portion 65 is fitted to the cover-fit endoscope 54, the cover holder 6 holds, by its arm 6a, a later-described mouth portion of the insert cover portion 65. This enables the endoscope to be held without touching the cover 53 by a hand, which is desirable from a hygienic standpoint. Also, the fitting operation is made easier.

As shown in FIG. 6, the insert cover portion 65 is of an elongate shape and has a mouth portion for fixing an endoscope operating unit (hereinafter abbreviated as a mouth portion) 65a at the proximal end and a distal end portion 65b which are both formed of hard material. The region of the insert cover portion 65 between the mouth portion 65a and the distal end portion 65b is covered with an insert cover sheath 65c for isolating the inner space from the external environment.

The insert cover sheath 65e is a pliable tube having the multi-layered, e.g., two-layered, structure and made of polytetrafluoroethylene sheets' each being elongated. Of the two layers, an inner layer 72 is elongated in an axial direction, for example, and an outer layer 73 is elongated in a different direction (e.g., a circumferential direction) from the inner layer 72. The elongated polytetrafluoroethylene has directivity in the tearing strength. With the above construction, since two layers elongated in different directions are laminated, these layers complement each other to provide a high degree of the tearing strength in all directions. Note that the two layers may be joined together by bonding or heating.

The insert cover sheath 65c having the above construction is less likely to tear and ensures safety even when a large force is imposed upon, for example, insertion/extraction of the endoscope. It is therefore possible to prevent contamination caused by tearing of the insert cover sheath 65c.

Further, the insert cover portion 65 has formed therein an endoscope insertion channel 68 allowing the insert 57 be inserted through the same. On the proximal end side of the endoscope insertion channel 68, an opening for inserting the insert 57 therethrough is formed in the mouth portion 65a. The opening of the endoscope insertion channel 68 is formed to have such a diameter that the mouth portion 65a closely contacts the endoscope insert 57. The endoscope insertion channel 68 is substantially closed at the distal end portion 65b of the insert cover portion 65. Thus, the endoscope insertion channel 68 accepts the insert 57 of the cover-fit endoscope 54 in such a manner as to isolate it from the external environment.

In the endoscope insertion channel 68, there are inserted an air supply line 69, a water supply line 70 and a suction line 71, these lines serving as channels. The air supply line 69, the water supply line 70 and the suction line 71 are of the two-layered structure similar to the insert cover sheath 65c of the insert cover portion 65, Those lines 69, 70, 71 each have one end open at the distal end portion 65b of the insert cover portion 65, and have the other end further extended from the mouth portion 65a toward the proximal side. The proximal end of each line is open and provided with a cover sheet 40, as a channel cover, shown in FIG. 8.

The air supply line 69, the water supply line 70 and the suction line 71 are inserted through the line insertion channel 64 formed in the cover-fit endoscope 54 and further extended beyond the opening 63a of the connector 63.

At the distal end portion 65b of the insert cover portion 65, as shown in FIG. 5, transparent windows 74, 75a, 75b are provided to close the distal end of the endoscope insertion channel 68. These windows 74, 75a, 75b are arranged at positions respectively facing the observation optical system 62 and the illumination optical systems 61, 61 of the cover-fit endoscope 54.

Also, at the distal end portion 65b of the insert cover portion 65, there are formed an air supply nozzle 76a and a water supply nozzle 76b both opened toward the window 74, and an opening 77. The air and water supply nozzles 76a, 76b are connected in fluid communication with respective distal ends of the air supply line 69 and the water supply line 70. The opening 77 is connected in fluid communication with the suction line 70.

As shown in FIG. 5, the air supply line 69 is connected at its proximal open end in fluid communication with the air supply source (not shown) of the fluid controller 9. The water supply line 70 is connected at its proximal open end in fluid communication with the air supply source via a water supply tank 33 as the water supply source. Further, the suction line 71 is connected at its proximal open end in fluid communication with a suction bottle (not shown) and a suction source (not shown).

The mouth portion 65a is provided with an appliance insertion inlet 41 and an expansion tube mouth 35 projecting from opposite sides. The expansion tube mouth 35 has its inner passage communicated with the endoscope insertion channel 68. An expansion tube 36 connected to the expander 10 is in turn releasably connected the expansion tube mouth 35.

The appliance insertion inlet 41 is projecting rearward in an axial direction of the insert cover portion 65. An inner passage of the appliance insertion inlet 41 is open at a projected end and communicated at the other end with the suction line 71, for example. Thus, the suction line 71 doubles as an appliance channel in the distal end side.

At the projected end of the appliance insertion inlet 41, a substantially tubular appliance plug 42 is provided integrally with the appliance insertion inlet 41.

FIG. 8 shows a first state and a second state of the cover sheet 40 attached to the end of each line.

Figure 8A:
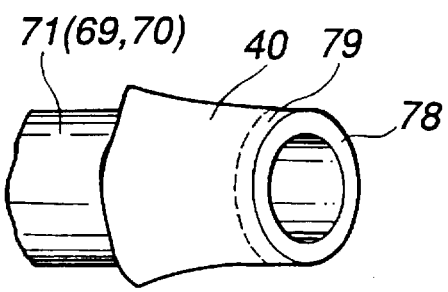

In the first state of FIG. 8(a), one end of the cylindrical cover sheet 40 is fixed to an end 78 of each of the lines 69, 70, 71. Reference numeral 79 denotes an end area where one end of the cover sheet 40 is fixed to the line end 78. Thus, the cover sheet 40 is integrally attached to each line end.

Figure 8B:
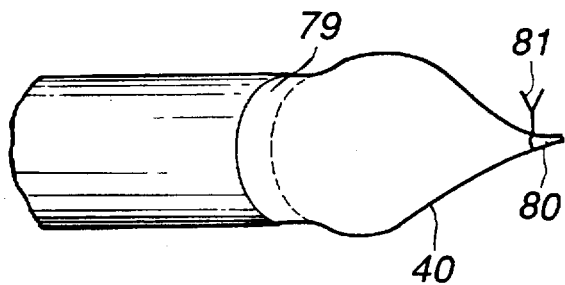

In the second state of FIG. 8(b), the cover sheet 40 is folded back about the fixed end area 79 to extend over the line end 78 of each of the lines 69, 70, 71. Thus, the other end 80 of the cover sheet 40 is closed by a clip 81.

With such an arrangement, the cover sheet 40 is held in the first state when the cover-fit endoscope 54 is fitted to the insert cover portion 65 or during examination.

More specifically, the lines 60, 70, 71 in the insert cover portion 65 are inserted through the line insertion channel 64 of the cover-fit endoscope 54. At the same time as this insertion, the insert cover sheath 65c covers the endoscope insert 57 so that the insert cover portion 65 fits over the endoscope insert. In a condition of completely inserting and fitting the insert cover portion 65, the lines 60, 70, 71 are projecting through the opening 63a of the endoscope connector 63. Then, the lines 60, 70, 71 are connected to the fluid controller 9 for fluid communication.

Incidentally, during insertion or extraction of the endoscope insert, channel expanding air is supplied to the insert cover portion 65 via the expansion tube 36 connected to the expander 10.

The cover-fit endoscope 54 is connected to the light source unit 7 and the video processor 8 in the cart 5. The other components of the cover 53 are fitted over the cover-fit endoscope 54 for covering the same in a watertight manner. The cover and the endoscope are thus combined into the cover fitted type endoscope 52 which is subsequently used for endoscope examination.

After examination, to remove the cover-fit endoscope 54 out of the insert cover portion 65, the air supply line 69, the water supply line 70 and the suction line 71 are first disconnected from the fluid controller 9. Then, the cover sheets 40 are folded back into the second state so that the open ends of the air supply line 69, the water supply line 70 and the suction line 71 are covered and closed by the cover sheets 40. Thereafter, the cover-fit endoscope 54 is removed out of the insert cover portion 65. At this time, as mentioned above, the respective ends of the air supply line 69, the water supply line 70 and the suction line 71 are closed. Accordingly, filth and so on from are prevented from leaking the open end 78 of each line, resulting in no fear of the cover-fit endoscope 54 being contaminated.

Then, only the contaminated cover 53 is discarded, while the cover-fit endoscope is left clean. Therefore, the cover-fit endoscope 54 can be fitted with a new sterilized cover and used again for next examination or treatment without the need of washing and disinfection.

With this embodiment, since the open ends of the lines 69, 70, 71 are tightly closed by the cover sheets 40 when removing the cover-fit endoscope 54 after examination, filth and so on are prevented from leaking out of any of the line ends 78, which eliminates a fear of infection and keeps the process in a hygienic condition. In addition, this embodiment eliminates the need for washing and disinfecting endoscopes, and also enables continual use of endoscopes.

Figure 9:
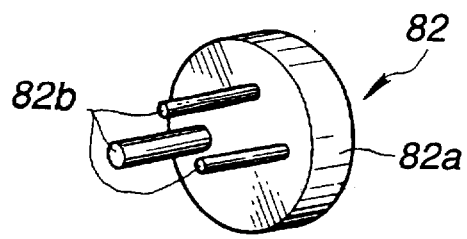
FIG. 9 is a perspective view of a line cover according to a fourth embodiment of the present invention.

FIG. 9 is a perspective view of a line cover according to a fourth embodiment of the present invention.

This fourth embodiment is different from the third embodiment in that a line cover for sealing the proximal end opening of each of the air supply line 69, the water supply line 70 and the suction line 71. A plug member 82 shown in FIG. 9 as the line cover is configured to seal the proximal end openings of the three lines.

The plug member 82 comprises a circular disk 82a and three cylinders 82b projecting from the circular disk 82a. These three cylinders 82b are formed to have outer diameters slightly larger than inner diameters of the air supply line 69, the water supply line 70 and the suction line 71, respectively. In other words, when fitted to the lines, the plug member 82 closes all the lines in a watertight manner.

After examination, to remove the cover-fit endoscope 54 out of the insert cover portion 65, the air supply line 69, the water supply line 70 and the suction line 71 are first disconnected from the fluid controller 9. Then, the cylinders 82b of the plug member 82 are inserted to the respective proximal end openings of the lines 69, 70, 71. Thereafter, the cover-fit endoscope 54 is removed out of the insert cover portion 65. At this time, as mentioned above, the respective ends of the air supply line 69, the water supply line 70 and the suction line 71 are sealed. With this embodiment, accordingly, filth and so on is prevented from leaking from any line ends, with the result of no fear of contaminating the cover-fit endoscope 54. The other construction, operation and advantages are similar to those in the third embodiment and will not be described again.

Figure 10:
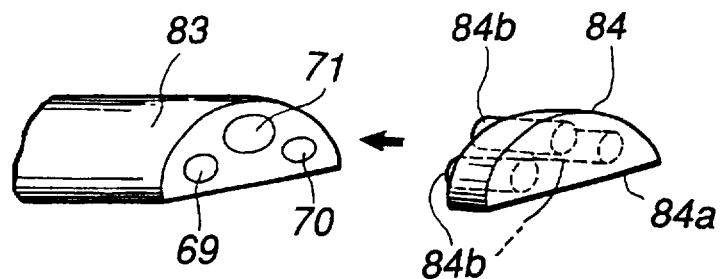
FIG. 10 is a perspective view of a line cover according to a fifth embodiment of the present invention.

FIG. 10 is a perspective view of a line cover according to a fifth embodiment of the present invention.

This fifth embodiment is different from the third embodiment in the structure of the three lines and the construction of the line cover for sealing the line ends. While the air supply line 69, the water supply line 70 and the suction line 71 are separate members in the third embodiment, they are formed in a one-piece semilunar multi-lumen tube 83 in this fifth embodiment.

A plug member 84 shown in FIG. 10 as the line cover comprises a semilunar disk 84 a having the same outer sectional configuration as the multi-lumen tube 83, and three cylinders 84b projecting from the semilunar disk 82a. These three cylinders 84b are formed to have outer diameters slightly larger than inner diameters of the air supply line 69, the water supply line 70 and the suction line 71, respectively. Also, the three cylinders 84b are arranged to align with the air supply line 69, the water supply line 70 and the suction line 71 formed in the multi-lumen tube 83, respectively. In other words, when fitted to the multi-lumen tube 83, the plug member 84 closes all the lines in a watertight manner.

After examination, to remove the cover-fit endoscope 54 out of the insert cover portion 65, the air supply line 69, the water supply line 70 and the suction line 71 are first disconnected from the fluid controller 9. Then, the cylinders 84b of the plug member 84 are inserted into the respective proximal end openings of the lines 69, 70, 71. Thereafter, the cover-fit endoscope 54 is removed out of the insert cover portion 65.

At this time, as mentioned above, the respective ends of the air supply line 69, the water supply line 70 and the suction line 71 are closed by the plug member 84. With this embodiment, accordingly, filth and so on are prevented from leaking from any of the line ends, with the result of no fear of contaminating the cover-fit endoscope 54.

Further, since the plug member 84 and the multi-lumen tube 83 have the same outer sectional configuration, there is no fear that the plug member 84 may be dislodged at the time of removing the cover-fit endoscope 54.

Additionally, the plug member 84 may be provided integrally with but releasable from the multi-lumen tube 83 by using a connection arm, for example. This arrangement can prevent a risk of fitting the contaminated plug member by mistake.

The other construction, operation and advantages are similar to those in the third embodiment and will not be described again.

Figure 11:
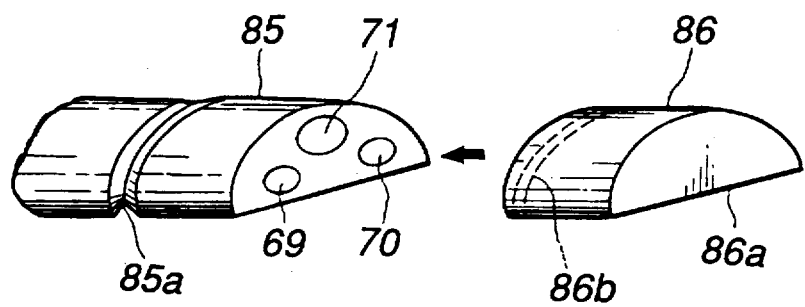
FIG. 11 is a perspective view of a line cover according to a sixth embodiment of the present invention.

FIG. 11 is a perspective view of a line cover according to a sixth embodiment of the present invention.

This sixth embodiment is different from the fifth embodiment in the end construction of the multi-lumen tube and the construction of the line cover for sealing the line ends. As with the fifth embodiment, the air supply line 69, the water supply line 70 and the suction line 71 are formed in a one-piece semilunar multi-lumen tube 85 in this sixth embodiment. As shown in FIG. 11, the multi-lumen tube 85 has a groove 85a formed entirely in the outer peripheral surface near its proximal end.

On the other hand, a line cap 86 as the line cover has the same outer sectional configuration as the multi-lumen tube 85, and a projection 86b engaging the groove 85a is formed on the inner peripheral surface of a bottom-equipped cylindrical body 86a dimensioned to cover the tube 85. When fitted to the multi-lumen tube 85, the line cap 86 closes all the lines in a watertight manner.

The other construction, operation and advantages are similar to those in the fifth embodiment and will not be described again.

Figure 12:
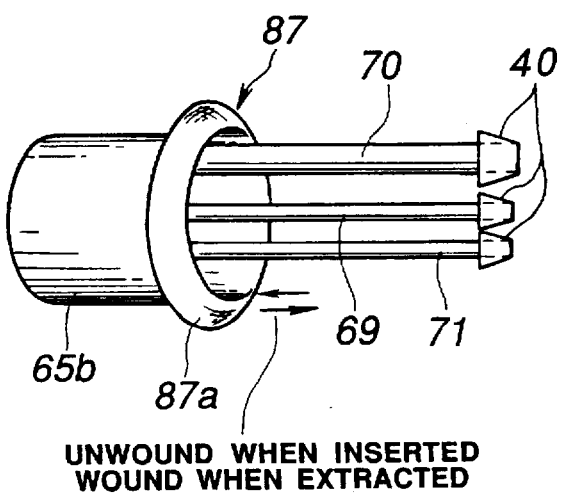
FIG. 12 is a view of showing the construction of an insert cover portion according to a first modification.

FIG. 12 is a view of showing the construction of an insert cover portion according to a first modification.

An insert cover portion 87 shown in FIG. 12 is modified in that the mouth portion 65a is not present or it is separable from an insert cover sheath 87a. The insert cover sheath 87a can be wound around or unwound from the side of the distal end portion 65b or the mouth portion 65a.

As shown in FIG. 12, the insert cover sheath 87a of the insert cover portion 87 is wound around the side of the distal end portion 65b beforehand. In this condition, the lines are inserted through the line insertion channel of the cover-fit endoscope 54. The insert cover sheath 87a is then unwound so that the insert cover sheath 87a fits over the insert 57 of the cover-fit endoscope 54. With this first modification, the cover-fit endoscope 54 can be easily inserted and extracted without needing the expander 10. The other construction, operation and advantages are similar to those in the above embodiment and will not be described again.

Figure 13:
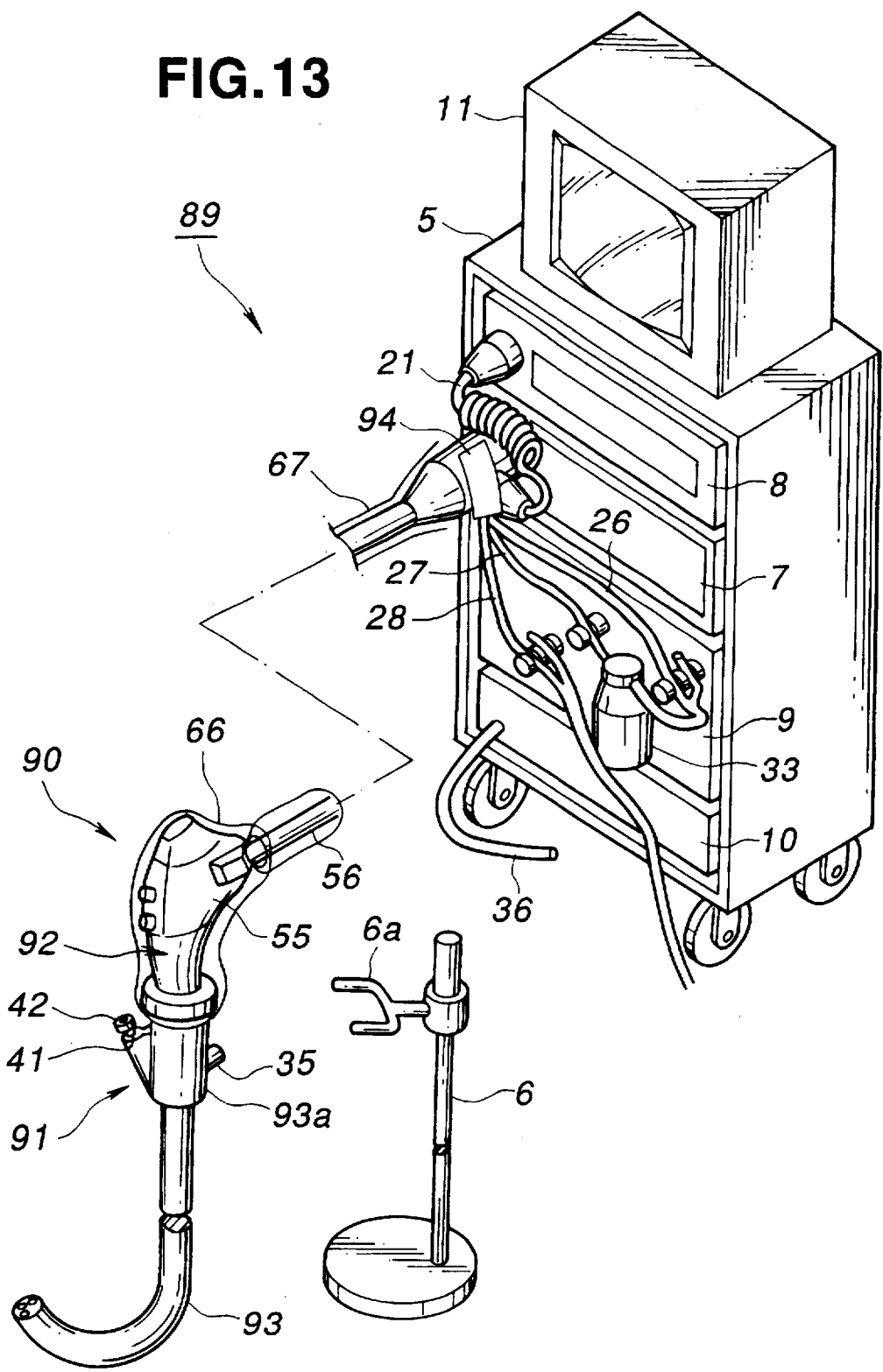
Figure 14A:
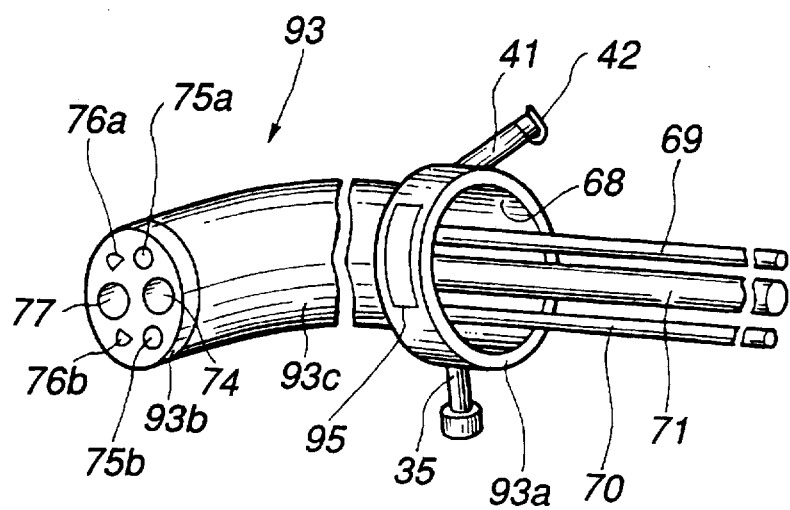
FIG. 14(a) is an appearance view of a channeled endoscope cover.
Figure 14B:
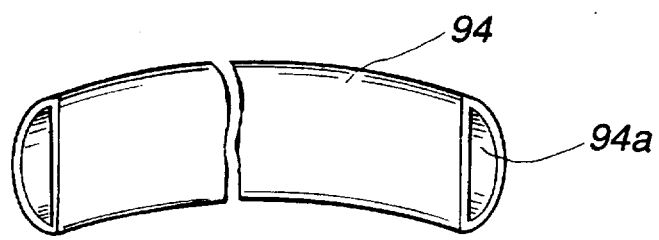
FIG. 14(b) is an appearance view of a line cover tube.
Figure 14C:
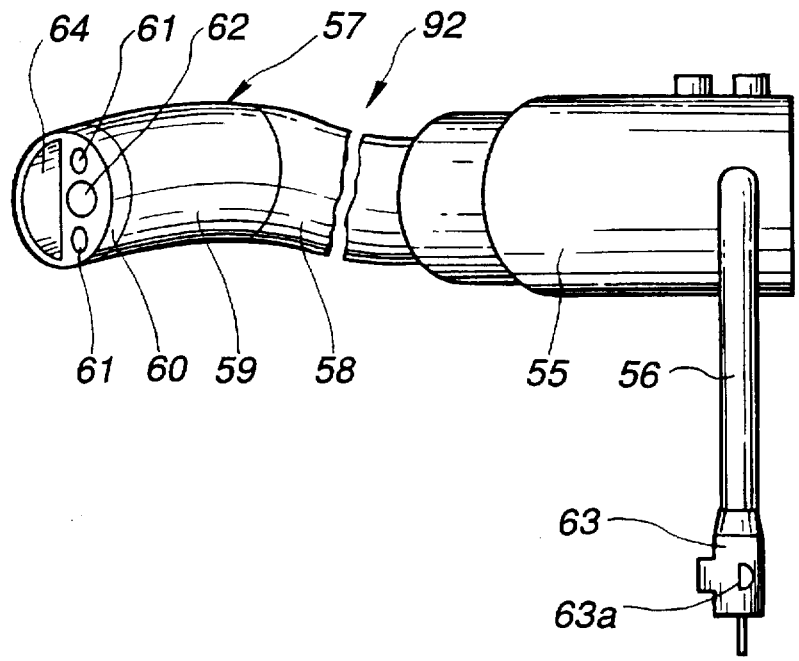
FIG. 14(c) is an appearance view of an endoscope to be fitted with the channeled endoscope cover.
Figure 15:
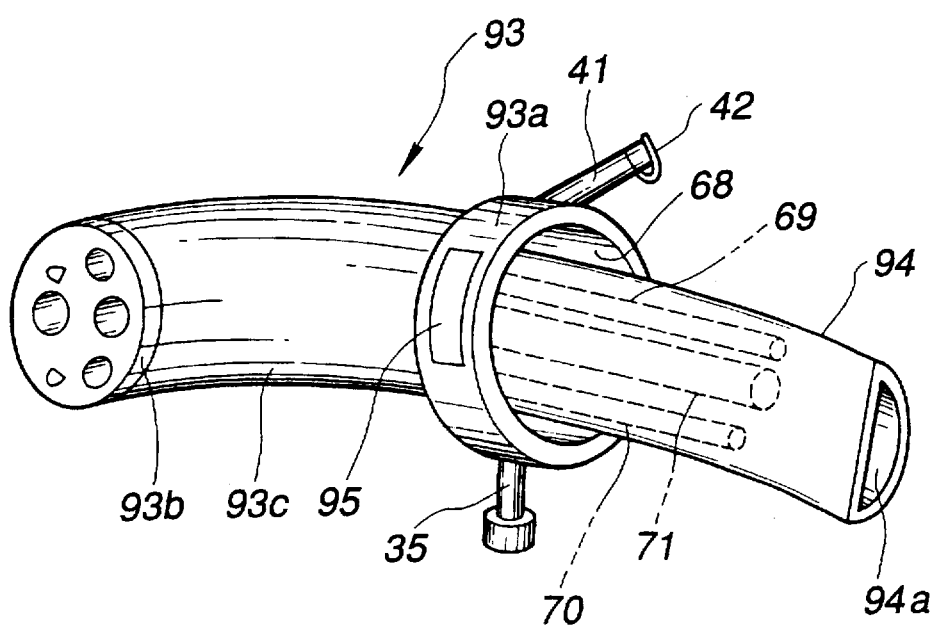
Figure 16:
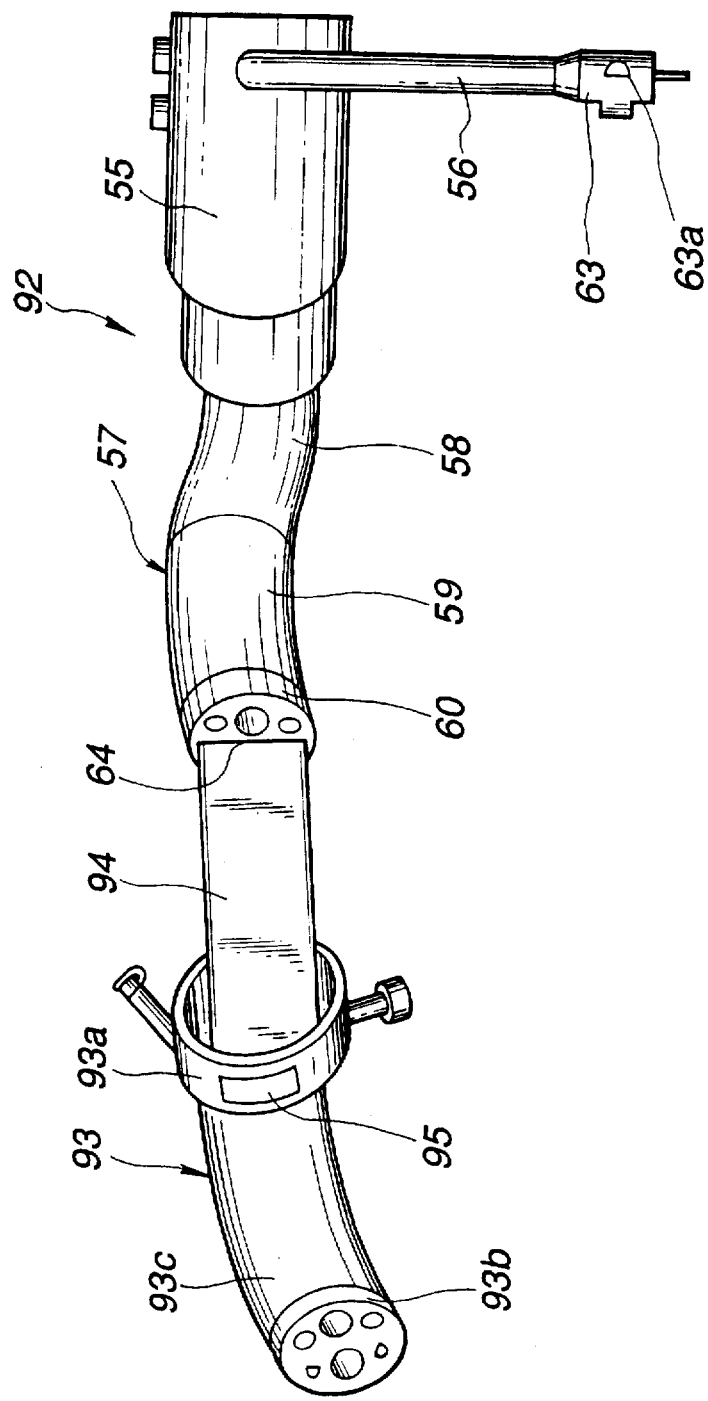
Figure 17:
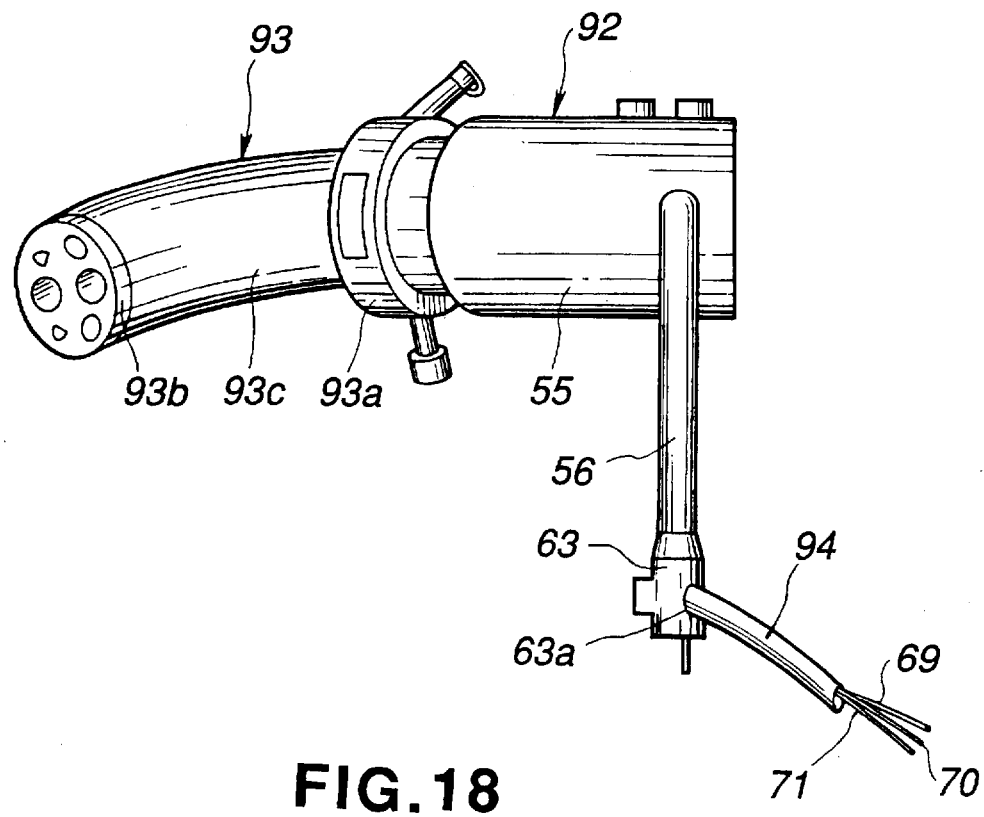
Figure 18:
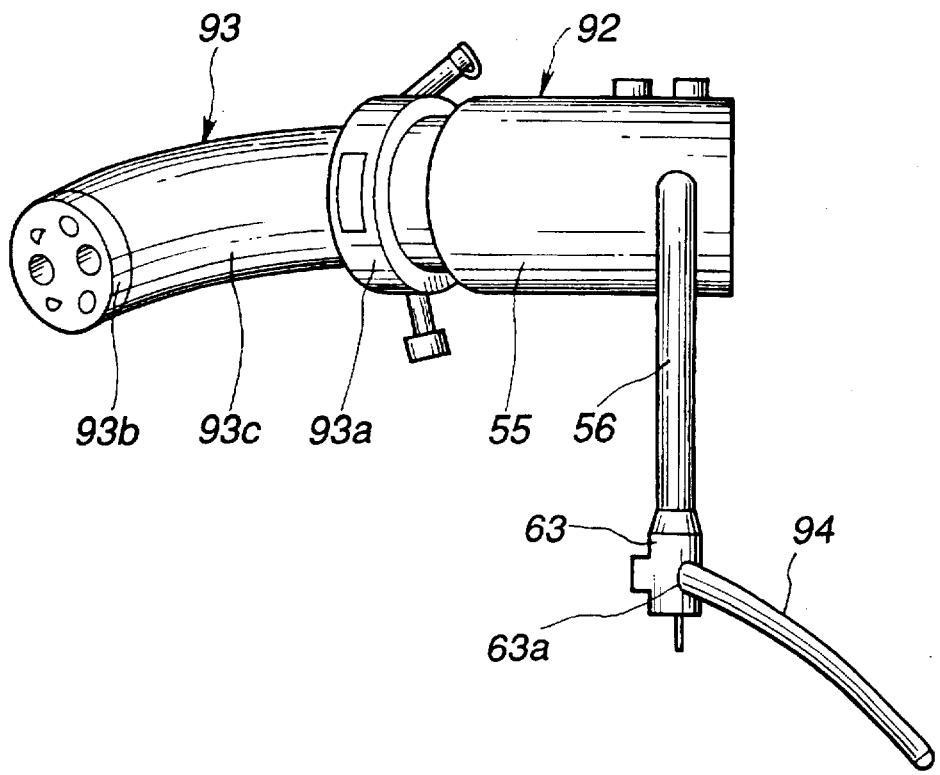

FIGS. 13 to 22 relate to a seventh embodiment of the present invention in which FIG. 13 is an overall appearance view of a channeled endoscope cover fitted type endoscope apparatus, FIG. 14(a) is an appearance view of a channeled endoscope cover, FIG. 14(b) is an appearance view of a line cover tube, FIG. 14(c) is an appearance view of an endoscope to be fitted with the channeled endoscope cover, FIG. 15 is an explanatory view showing a state that a line cover tube is fitted to lines in an insert cover portion, FIG. 16 is an explanatory view showing a state that the cover is being fitted to the cover-fit endoscope, FIG. 17 is an explanatory view showing a state that the cover has been completely fitted over the cover-fit endoscope, and FIG. 18 is an explanatory view showing a state when the cover-fit endoscope is extracted from the cover.

Figure 19:
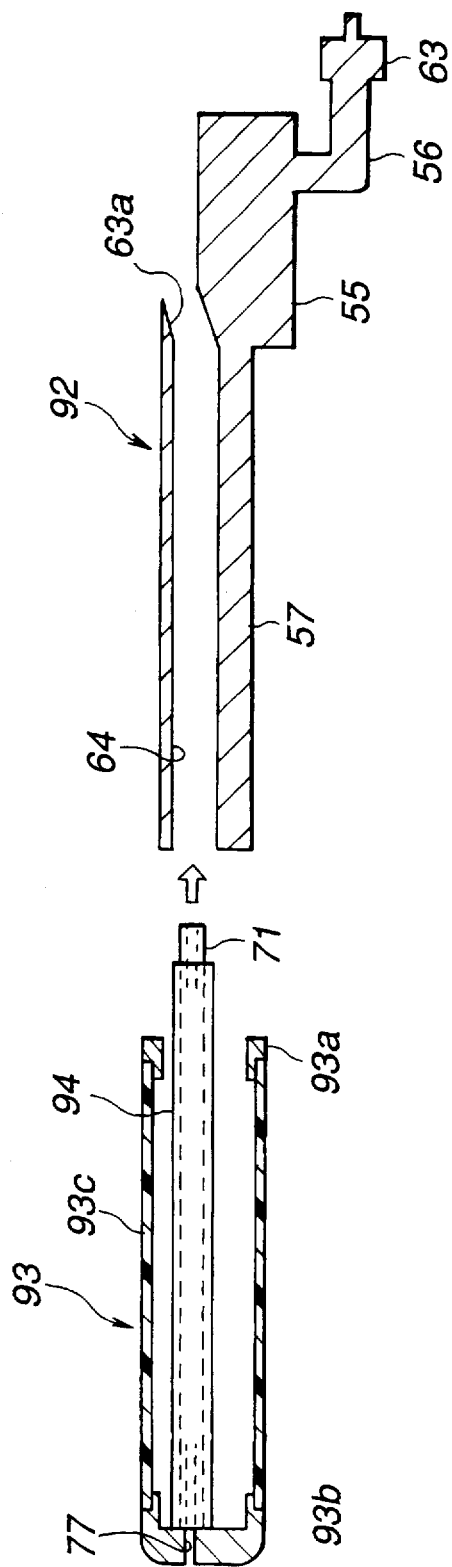
Figure 20:
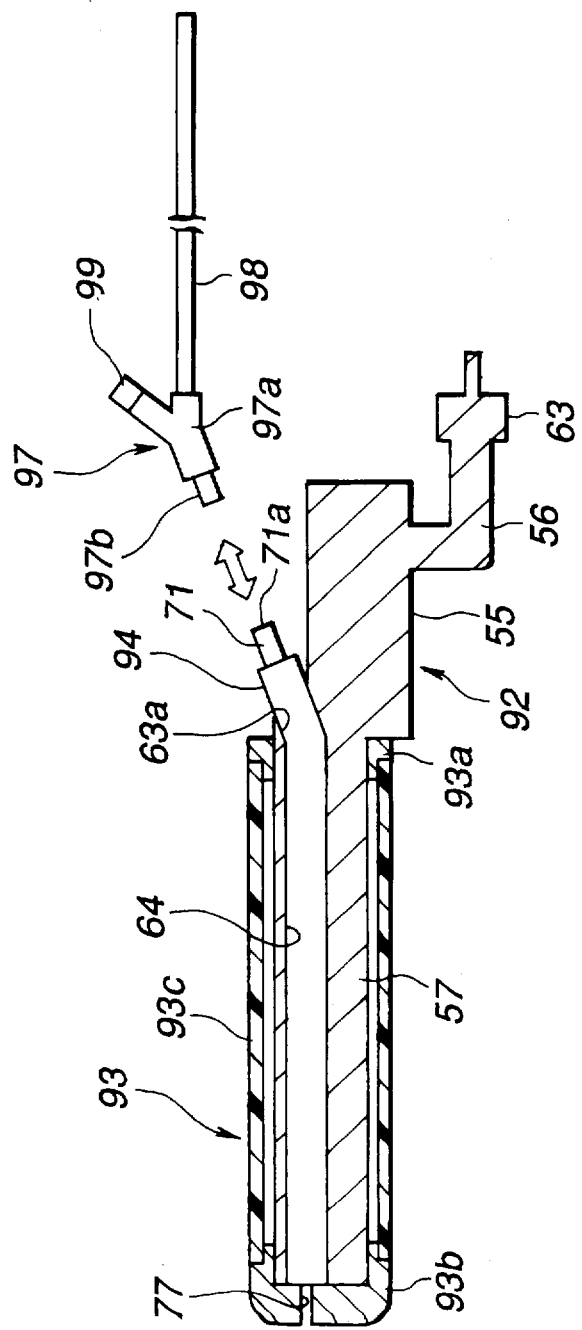
FIG. 20 is a side sectional view showing the modification of the cover fitted type endoscope.
Figure 21:
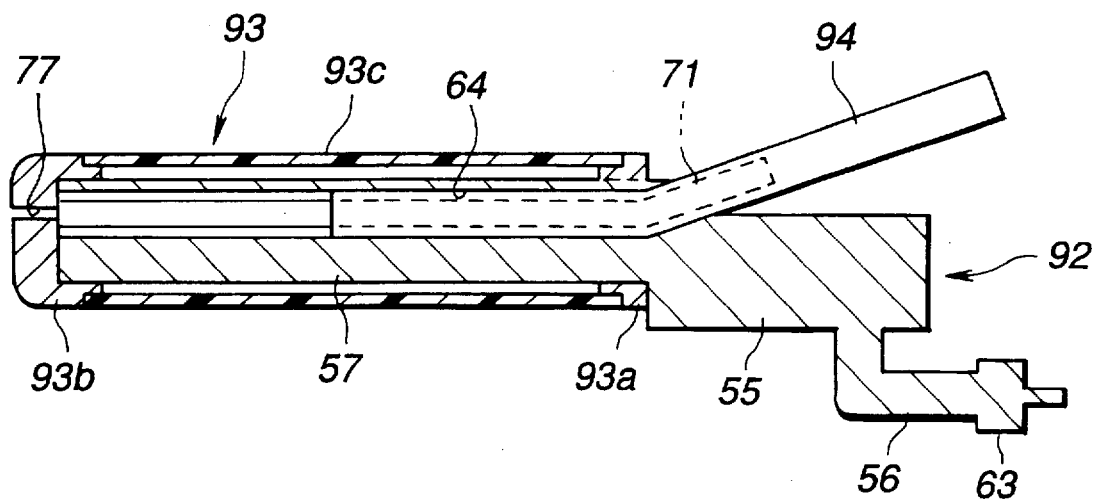
FIG. 21 is a side sectional view for explaining the modification of the cover fitted type endoscope.
Figure 22:
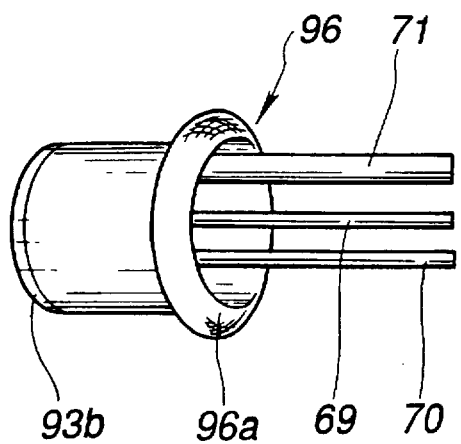
FIG. 22 is a view showing the construction of an insert cover portion according to a second modification.

Further, FIG. 19 is a side sectional view showing a modification of the cover fitted type endoscope, FIG. 20 is a side sectional view showing the modification of the cover fitted type endoscope, FIG. 21 is a side sectional view for explaining the modification of the cover fitted type endoscope, and FIG. 22 is a view of showing the construction of an insert cover portion according to a second modification.

An endoscope apparatus 89 shown in FIG. 13 includes a channeled endoscope cover fitted type endoscope (hereinafter abbreviated as a cover fitted type endoscope) 90.

The cover fitted type endoscope 90 comprises, in combination, a channeled endoscope cover (hereinafter abbreviated as a cover) 91 and an endoscope to be fitted with the channeled endoscope cover (hereinafter abbreviated as a cover-fit endoscope) 92. The cover 91 covers an insert etc. of the cover-fit endoscope 92 to eliminate any need for washing and disinfecting the endoscope after examination.

The endoscope apparatus 89 comprises the cover fitted type endoscope 90, a cart 5 for housing various peripheral equipment therein to which the cover fitted type endoscope 90 is connected, and a cover holder 6 for holding the cover fitted type endoscope 90.

As shown in FIG. 13, the cart 5 for housing various peripheral equipment therein houses, for instance, the light source unit 7, the video processor 8, the fluid controller 9, and the expander 10. The monitor 11 is placed on a top plate of the cart 5.

The light source unit 7 supplies an illumination light to the cover-fit endoscope 92 of the cover fitted type endoscope 90. The video processor 8 is connected to the electronic covered-fit endoscope 92 for converting an electric signal from the endoscope 92 into a standard video signal and outputting it to the monitor 11. The monitor 11 receives the video signal and displays an endoscope image.

The fluid controller 9 carries out supply of air and water, etc. through later-described lines provided in the cover 91. To this end, the fluid controller 9 includes a water supply source 33, an air supply source (not shown), etc. and the lines connected to these water and air supply sources are controlled by solenoid valves to selectively open and close.

The expander 10 supplies air to the cover 91 for expanding the same. This expansion of the cover 91 allows the cover-fit endoscope 92 to be easily inserted and extracted.

The cover-fit endoscope 92 comprises, as shown in FIG. 14(c), an operating unit 55, a universal cord 56 extending from one side of the operating unit 55, and an insert 57 connected to the operating unit 55. The insert 57 of the cover-fit endoscope 92 is formed into an elongate cylindrical shape. Accordingly, the same bending structure as used in conventional non-covered endoscopes can also be applied to the cover-fit endoscope 92.

The insert 57 of the cover-fit endoscope 92 comprises, as shown in FIG. 14(c), a flexible tube portion 58, a bendable bending portion 59, and a hard distal end portion 60 arranged in this order from its proximal end adjacent the operating unit 55 toward its distal end.

In the distal end portion 60 of the cover-fit endoscope 92, there are arranged illumination optical systems 61, 61 and an objective optical system 62.

An exiting end of a light guide fiber (not shown) is arranged at rear ends of the illumination optical systems 61, 62, the light guide fiber being inserted through the insert 57, the operating unit 55 and the universal cord 56.

A connector 63 is provided at a proximal end of the universal cord 56 and releasably connected to the light source unit 7. The illumination light from the light source unit 7 is introduced to an incoming end of the light guide fiber.

In the distal end portion 60 of the cover-fit endoscope 92, there is formed an opening of a line insertion channel 64 having a semicircular or D-shaped cross-section. A plurality of later-described lines formed in the cover 91 are inserted through the line insertion channel 64. The line insertion channel 64 is communicated with a proximal end opening 63a formed in one side of the connector 63 through the insert 57, the operating unit 55 and the universal cord 56.

At a rear end of the objective optical system 62, there is arranged a solid state image sensor (not shown) for converting an incoming optical image into an electric signal. The electric signal output from the solid state image sensor is applied to the video processor 8 via a signal cord 21 extending from one side of the connector 63 shown in FIG. 13.

The cover 91 to be fitted over the cover-fit endoscope 92 comprises, as shown in FIG. 13, an insert cover portion 93, an operating unit cover portion 66, and a universal cord cover portion 67. The insert cover portion 93 of the cover 91 covers the insert 57 of the cover-fit endoscope 92. The operating unit cover portion 66 of the cover 91 covers the operating unit 55 of the cover-fit endoscope 92. Further, the universal cord cover portion 67 of the cover 91 covers the universal cord 56 of the cover-fit endoscope 92. The cover-fit endoscope 92 is entirely fitted with the cover 91 and used for examination in a watertight covered condition.

Additionally, when the insert cover portion 93 is fitted to the cover-fit endoscope 92, the cover holder 6 holds, by its arm 6a, a later-described mouth portion of the insert cover portion 93. This enables the endoscope to be held without touching the cover 91 by a hand, which is desirable from a hygienic standpoint. Also, the fitting operation is made easier.

As shown in FIG. 14(a), the insert cover portion 93 has an elongate shape and a mouth portion for fixing an endoscope operating unit (hereinafter abbreviated as a mouth portion) 93a at the proximal end and a distal end portion 93b which are both formed of hard material. The region of the insert cover portion 93 between the mouth portion 93a and the distal end portion 93b is covered with an insert cover sheath 93c for isolating the inner space from the external environment.

Further, the insert cover portion 93 has an endoscope insertion channel 68 formed therein allowing the insert 57 be inserted through the same. On the proximal end side of the endoscope insertion channel 68, an opening for inserting the insert 57 therethrough is formed in the mouth portion 93a. The opening of the endoscope insertion channel 68 is formed to have such a diameter that the mouth portion 93a closely contacts the endoscope insert 57. The endoscope insertion channel 68 is substantially closed at the distal end portion 93b of the insert cover portion 93. Thus, the endoscope insertion channel 68 accepts the insert 57 of the cover-fit endoscope 92 in such a manner as to isolate it from the external environment.

In the endoscope insertion channel 68, there are inserted an air supply line 69, a water supply line 70 and a suction line 71.

Those lines 69, 70, 71 each have one end open at the distal end portion 93b of the insert cover portion 93, and have the other end further extended from the mouth portion 93a toward the proximal side. The proximal end of each line is open.

At the distal end portion 93b of the insert cover portion 93, as shown in FIG. 13, transparent windows 74, 75a, 75b are provided to close the distal end of the endoscope insertion channel 68. These windows 74, 75a, 75b are arranged at positions respectively facing the observation optical system 62 and the illumination optical systems 61, 61 of the cover-fit endoscope 92.

Also, at the distal end portion 93b of the insert cover portion 93, there are formed an air supply nozzle 76a and a water supply nozzle 76b both opened toward the window 74, and an opening 77. The air and water supply nozzles 76a, 76b are connected in fluid communication with respective distal ends of the air supply line 69 and the water supply line 70. The opening 77 is connected in fluid communication with the suction line 70.

On the other hand, a line cover tube 94 shown in FIG. 14(b) is formed of from a thin-wall tubular member having a semicircular or D-shaped cross-section, and is sized such that it can be inserted through the line insertion channel 64. The line cover tube 94 is slightly shorter than the air supply line 69, the water supply line 70 and the suction line 71, but slightly longer than the line insertion channel 64. The air supply line 69, the water supply line 70 and the suction line 71 are inserted through a cavity 94a of the line cover tube 94. Further, the line cover tube 94 is slidable in a lengthwise direction of the lines. Additionally, the line cover tube 94 may be of the two-layered structure similarly to the insert cover sheath 65c in the third embodiment. The resulting advantage is as mentioned before.

The air supply line 69, the water supply line 70 and the suction line 71 are inserted through the line insertion channel 64 in the cover-fit endoscope 92 in a condition in which it has been fitted to the line cover tube 94, as shown in FIG. 15.

The lines 60, 70, 71 fitted to the line cover tube 94 and inserted through the line insertion channel 64 are further extended from the opening 63a of the endoscope connector 63.

Note that the overall length of the line cover tube 94 may be almost equal to that of each line. Alternatively, the tube 94 may be slightly longer than each line when rewound in use after completion of the insertion.

As an alternative, the line cover tube 94 may have a length almost equal to the length by which each line is projecting from the mouth portion 93a of the insert cover portion 93, or it may sized only enough to cover the proximal open ends of the lines. In the latter case, the tube 94 is preferably configured to tightly accept the line ends for preventing its slip-off at the time of insertion/extraction.

As shown in FIG. 13, the air supply line 69 is connected at its proximal open end in fluid communication with the air supply source (not shown) of the fluid controller 9. The water supply line 70 is connected at its proximal open end in fluid communication with the air supply source via a water supply tank 33 as the water supply source. Further, the suction line 71 is connected at its proximal open end in fluid communication with a suction bottle (not shown) and a suction source (not shown).

The mouth portion 93a of the insert cover portion 93 is provided with an appliance insertion inlet 41 and an expansion tube mouth 35 projecting from opposite sides. The expansion tube mouth 35 has its inner passage communicated with the endoscope insertion channel 68. An expansion tube 36 connected to the expander 10 is in turn releasably connected to the expansion tube mouth 35.

The appliance insertion inlet 41 is projecting rearward in an axial direction of the insert cover portion 93. An inner passage of the appliance insertion inlet 34 is open at a projected end and communicated at the other end with the suction line 71, for example. Thus, the suction line 71 doubles as an appliance channel in the distal end side.

At the projected end of the appliance insertion inlet 41, a substantially tubular appliance plug 42 is provided integrally with the appliance insertion inlet 41.

Further, a seal 95 impregnated with cobalt chloride is pasted to the mouth portion 93a of the insert cover portion 93. Once the cover 91 is taken out of a sterilized package (not shown) for containing the cover and other components, cobalt chloride gradually changes its color to red while absorbing moisture. It can be thus confirmed from color change of the seal 95 how long before the cover has been taken out of the sterilized package. The long amount of time in an unpacked condition increases the possibility that germs may deposit on the cover. This enables the possibly contaminated cover to be discarded without using it unknowingly, which results in a higher level of safety.

The seal 95 may be attached to the insert cover sheath A reagent impregnated in the seal 95 may be a protein analyzing reagent such as ninhydrin, for example. When the insert cover sheath is inserted to the body cavity, the reagent reacts with the protein in the body to change its color. Accordingly, it can be determined at a glance whether the cover 91 has been once used for examination or not. As a result, reuse of the contaminated cover can be prevented, thereby ensuring that the cover is used in hygienic and safe conditions.

In this embodiment thus constructed, the line cover tube 94 is first fitted to the lines 69, 70, 71 of the insert cover portion 93. At this time, the line cover tube 94 is abutted against the inner wall of the cover distal end portion 93b (see FIG. 19). Then, as shown in FIG. 16, the line cover tube 94 covering the lines 60, 70, 71 is inserted through the line insertion channel 64 of the cover-fit endoscope 92. On this occasion, the open ends of the lines 69, 70, 71 are also inserted through the channel 64, but they are kept isolated from the channel 64 by the presence of the line cover tube 94. At the same time as such insertion of the line cover tube 94, the insert cover sheath 93c covers the endoscope insert 57 so that the cover-fit endoscope 92 is fitted to the cover 93. Then, the endoscope insert 57 is continuously inserted to the cover 93 until its distal end strikes against the inner wall of the cover distal end portion 93b. In a condition that the endoscope insert 57 has been completely inserted and fitted, the line cover tube 94 is extended from the opening 63a of the endoscope connector 63, as shown in FIG. 17. Also, the lines 69, 70, 71 are projected out of the proximal end opening of the line cover tube 94. In such a condition, the lines 69, 70, 71 are connected to be in communication with the fluid controller 9, as shown in FIG. 13.

Incidentally, during insertion or extraction of the endoscope insert, channel expanding air is supplied to the insert cover portion 93 via the expansion tube 36 connected to the expander 10.

The cover-fit endoscope 92 is connected to the light source unit 7 and the video processor 8 in the cart 5. The other components of the cover 91 are fitted over the cover-fit endoscope 92 for covering the same in an watertight manner. The cover and the endoscope are thus combined into the cover fitted type endoscope 90 which is subsequently used for endoscope examination.

After examination, to remove the cover-fit endoscope 92 out of the insert cover portion 93, the air supply line 69, the water supply line 70 and the suction line 71 are first disconnected from the fluid controller 9. Then, the line cover tube 94 is slid toward the open ends of the air supply line 69, the water supply line 70 and the suction line 71. The open ends of the lines 69, 70, 71 are thereby covered by the line cover tube 94, as shown in FIG. 18. Subsequently, the cover-fit endoscope 92 is removed out of the insert cover portion 93. During this step, at the time of extracting the three lines from the line insertion channel 64 of the endoscope insert, the open ends of the respective lines are kept isolated from the line insertion channel 64 of the endoscope insert by the line cover tube 94. Accordingly, even if some filth leaks through the line open ends, there is no fear that the line insertion channel 64 of the cover-fit endoscope 92 might be contaminated.

Then, only the contaminated cover 91 is discarded, while the cover-fit endoscope is left clean. Therefore, the cover-fit endoscope 92 can be fitted with a new sterilized cover and used again for next examination or treatment without the need of washing and disinfection.

With this embodiment, since the open ends of the lines 69, 70, 71 are isolated from the channel 64 at the time of removing the cover-fit endoscope 92 after examination, filth and so on are prevented from leaking out of any line open ends, which eliminates a fear of infection and keeps the process in safe and hygienic conditions. In addition, this embodiment eliminates the need for washing and disinfecting endoscopes, and also enables continual use of endoscopes.

Moreover, since the lines are first covered at their open ends by the line cover tube 94 and then inserted to the endoscope along with the line cover tube 94, there is also no possibility that filth and so on adhering to the endoscope may contaminate the line open ends conversely to the above case.

In a modification shown in FIGS. 18 to 21, the construction of the cover-fit endoscope is partly different from that of the above embodiment. While the line insertion channel 64 is extended to be communicated with the connector 63 in the above embodiment, the opening 63a of the line insertion channel 64 is located in the operating unit 55 in this modification, as shown in FIG. 19. Also, in this modification, a Y-branched tube 97 can be connected to a proximal open end 71a of the suction line 71, as shown in FIG. 20.

The Y-branched tube 97 comprises a branched tube body 97a and a distal joining tube 97b provided at a distal end of the branched tube body 97a. A proximal side suction line 98 is connected to one branched end of the branched tube body 97a. The fluid controller 9 is in turn connected to a proximal end of the proximal side suction line 98.

Further, a forceps plug 99 is releasably attached to an opening of the branched tube body 97a. An appliance can be inserted through the other branched end of the branched tube body 97a.

The distal joining tube 97b of the Y-branched tube 97 having the above construction is releasably connected to the proximal open end 71a of the suction line 71. Endoscope examination is carried out in a condition in which the Y-branched tube 97 is connected to the fluid controller 9.

Subsequent to the examination, the forceps plug 99, the Y-branched tube 97 and the proximal side suction line 98 are removed from the suction line 71 after disinfecting them and sucking air.

The proximal end of the suction line 91 is wiped by gauze impregnated with disinfecting alcohol. The reason is as follows. Because of air suction following the disinfection, the inner passages of the suction line 71 and the proximal end suction line 98 are cleaned over the entire length. However, in view of the case that the inner passage of the suction line 71 may not be sufficiently clean, it is desirable to perform additional disinfection. By so doing, germs can be prevented from spreading to the surroundings, which may otherwise occur when the distal joining tube 97b is extracted from the suction line 71. Incidentally, an attention must be paid to that, after disinfection, the used gauze may not touch the tube 94 and the operating unit 57 to avoid their counter contamination.

Thereafter, taking care not to touch the suction line 71, the projected proximal end of the line cover tube 94 is held by fingers and slid such that the end of the line cover tube 94 is spaced about 5 to 30 cm, for example, from the end face of the suction line 71, as shown in FIG. 21. After so sliding the line cover tube 94, the cover-fit endoscope 92 is extracted from the insert cover portion 93.

At the time of extracting the endoscope, the open end of the suction line 71 is kept isolated from the line insertion channel 64 of the endoscope by the presence of the line cover tube 94. Accordingly, even if some filth leaks through the line open end, there is no fear that the line insertion channel 64 of the cover-fit endoscope 92 might be contaminated.

During the extraction, the line cover tube 94 may shift a little toward the proximal side. However, since the tube 94 covers the suction line 71 over a substantial length, the tube 94 will not slip off from the suction line 71 before the suction line 71 is extracted out of the inner space of the line insertion channel 64.

FIG. 22 is a view showing the construction of an insert cover portion according to a second modification.

An insert cover portion 96 shown in FIG. 22 is modified so that the mouth portion 65a is not present or it is separable from an insert cover sheath 96a. The insert cover sheath 96a can be wound around or unwound from the side of the distal end portion 65b or the mouth portion 65a.

As shown in FIG. 22, the insert cover sheath 96a of the insert cover portion 96 is wound around the side of the distal end portion 65b beforehand. In this condition, the line cover tube 94 through which the lines have been inserted is inserted and fitted to the line insertion channel of the cover-fit endoscope 54. The insert cover sheath 96a is then unwound so that the insert cover sheath 96a fits over the insert 57 of the cover-fit endoscope 54. When extracting the insert 57, the insert cover sheath 96a is wound around the distal end portion 65b in a reversed manner to the above. With this modification, the cover-fit endoscope 54 can be easily inserted and extracted without needing the expander 10. The other construction, operation and advantages are similar to those in the above embodiment and will not be described again.

It should be noted that, in the foregoing embodiments, the cover-fit endoscope is not particularly limited to the above-explained electronic endoscope and may be an optical fiber endoscope or an ultrasonic endoscope.

Also, the cover package shown in the second embodiment can be used with the first embodiment and with other embodiments and modifications as well.

Further, in the cover-fit endoscopes in the foregoing embodiments and modifications, the line insertion channel 64 may be extended to the opening formed in the operating unit 55 instead of the opening 63a of the connector 63, similarly to the seventh embodiment.

It is apparent that a variety of different embodiment forms of the invention can be constituted based on the spirit of the invention. The invention is only limited by the attached claims and not restricted by any particular embodiment forms.

What is claimed is:

1. An endoscope system comprising:
   an endoscope cover having therein an endoscope insertion channel and at least one line which is detachably connected to an external device;
   an endoscope cover fitted type endoscope having an insertion portion at a distal end and an operating unit at a proximal end, said insertion portion being insertable through said endoscope insertion channel of said endoscope cover and which has a line insertion channel in said insertion portion through which said line is passed when said insertion portion of said endoscope is inserted through said endoscope insertion channel of said endoscope cover; and
   an isolation member for isolating the proximal end opening of said line of said endoscope cover from said line insertion channel of said endoscope when said endoscope is removed from said endoscope cover, said isolation member having an outer diameter which is less than an outer diameter of said line insertion channel of said endoscope, said isolation member acting to completely prevent passage of fluid from the proximal end opening of said line of said endoscope cover during the removal operation,
   said line insertion channel of said endoscope communicating with the outside through a cord extending from said operating unit of said endoscope,
   said line of said endoscope cover passing through said line insertion channel in said insertion portion and said operating unit of said endoscope and a cord and extended outwards, and the proximal open end of said line being detachably connected to an external device.

2. An endoscope system according to claim 1, wherein said line which is detachably connected to said external device is an air supply line or a water supply line or a suction line.

3. An endoscope system according to claim 2, wherein said suction line is separated into branches at the proximal side of said endoscope cover, and one of said branches is extended outwards from the proximal side of said endoscope cover so as to form an appliance insertion inlet.

4. An endoscope system according to claim 3, wherein said appliance insertion inlet is provided with a plug.

5. An endoscope system according to claim 1, wherein said external device to which the proximal end of said line of said endoscope cover is detachably connected is either one of an air supply source, a water supply source and a suction source.

6. An endoscope system according to claim 1, wherein said endoscope insertion channel of said endoscope cover is closed except for an opening for insertion at the proximal side thereof in order to isolate said endoscope inserted therethrough airtightly and watertightly from the external environment.

7. An endoscope system according to claim 6, wherein said endoscope insertion channel of said endoscope cover is provided with an expansion tube mouth at the proximal side thereof in order to supply air into said channel to expand it, said expansion tube mouth being connected via an expansion tube to an expander which is provided as an external device.

8. An endoscope system according to claim 1, wherein said endoscope cover comprises a sheath covering said endoscope insertion channel, said sheath having a multi-layered structure.

9. An endoscope system according to claim 1, wherein said isolation member is a plug member which is mounted to the proximal open end of said line of said endoscope cover, and said plug member is to be mounted to the proximal open end of said line of said endoscope cover when said endoscope is removed from said endoscope cover.

10. An endoscope system according to claim 1, wherein said isolation member is a line cover tube into which said line of said endoscope cover is inserted and which is inserted into said line insertion channel of said endoscope, and said line cover tube seals the proximal end opening of said line when said endoscope is removed from said endoscope cover.

11. An endoscope system according to claim 10, wherein said line cover tube is slidable in said line insertion channel of said endoscope in a lengthwise direction of said line.

12. An endoscope system comprising:
an endoscope cover having therein an endoscope insertion channel and at least one line which is detachably connected to an external device;
an endoscope cover fitted type endoscope having an insertion portion at a distal end and an operating unit at a proximal end, said insertion portion being insertable through said endoscope insertion channel of said endoscope cover and which has a line insertion channel in said insertion portion through which said line is passed when said insertion portion of said endoscope is inserted through said endoscope insertion channel of said endoscope cover; and
an isolation member for isolating the proximal end opening of said line of said endoscope cover from said line insertion channel of said endoscope when said endoscope is removed from said endoscope cover,
said line insertion channel of said endoscope communicating with the outside through a cord extending from said operating unit of said endoscope,
said line of said endoscope cover passing through said line insertion channel in said insertion portion and said operating unit of said endoscope and a Cord and extended outwards, and the proximal open end of said line being detachably connected to an external device,
wherein said endoscope cover comprises a sheath covering said endoscope insertion channel, said sheath having a multi-layered structure, and
wherein, of the two layers of said sheath, an inner layer is elongated in one direction, and an outer layer is elongated in a direction different from said direction of said inner layer.

13. An endoscope system comprising:
an endoscope cover having therein an endoscope insertion channel and at least one line which is detachably connected to an external device;
an endoscope cover fitted type endoscope having an insertion portion at a distal end and an operating unit at a proximal end, said insertion portion being insertable through said endoscope insertion channel of said endoscope cover and which has a line insertion channel in said insertion portion through which said line is passed when said insertion portion of said endoscope is inserted through said endoscope insertion channel of said endoscope cover; and
an isolation member for isolating the proximal end opening of said line of said endoscope cover from said line insertion channel of said endoscope when said endoscope is removed from said endoscope cover,
said line insertion channel of said endoscope communicating with the outside through a cord extending from said operating unit of said endoscope,
said line of said endoscope cover passing through said line insertion channel in said insertion portion and said operating unit of said endoscope and a cord and extended outwards, and the proximal open end of said line being detachably connected to an external device,
wherein said isolation member for isolating the proximal end opening of said line of said endoscope cover from said line insertion channel of said endoscope is a cover sheet of which one end is fixed to the vicinity of the proximal open end of said line of said endoscope cover, and the other end of said cover sheet is tightly closed to seal the proximal end opening of said line of said endoscope cover when said endoscope is removed from said endoscope cover.

14. An endoscope system comprising:
an endoscope cover having therein an endoscope insertion channel and at least one line which is detachably connected to an external device;
an endoscope cover fitted type endoscope having an insertion portion at a distal end and an operating unit at a proximal end, said insertion portion being insertable through said endoscope insertion channel of said endoscope cover and which has a line insertion channel in said insertion portion through which said line is passed when said insertion portion of said endoscope is inserted through said endoscope insertion channel of said endoscope cover; and
an isolation member for isolating the proximal end opening of said line of said endoscope cover from said line insertion channel of said endoscope when said endoscope is removed from said endoscope cover,
said line insertion channel of said endoscope communicating with the outside through a cord extending from said operating unit of said endoscope, said line of said endoscope cover passing through said line insertion channel in said insertion portion and said operating unit of said endoscope and a cord and extended outwards, and the proximal open end of said line being detachably connected to an external device, wherein said isolation member is a line cover tube into which said line of said endoscope cover is inserted and which is inserted into said line insertion channel of said endoscope, and said line cover tube seals the proximal end opening of said line when said endoscope is removed from said endoscope cover, and wherein said line cover tube has a length greater than said line insertion channel of said endoscope and less than said line of said endoscope cover.

* * * * *